United States Patent
Rawat et al.

(10) Patent No.: US 9,150,498 B2
(45) Date of Patent: Oct. 6, 2015

(54) PROCESS FOR THE PREPARATION OF OSELTAMIVIR AND METHYL 3-EPI-SHIKIMATE

(71) Applicant: Council of Scientific & Industrial Research, New Delhi (IN)

(72) Inventors: Varun Rawat, Pune (IN); Soumen Dey, Pune (IN); Sudalai Arumugam, Pune (IN)

(73) Assignee: Council of Scientific & Industrial Research (IN)

( * ) Notice: Subject to any disclaimer, the term of this patent is extended or adjusted under 35 U.S.C. 154(b) by 0 days.

(21) Appl. No.: 14/354,478

(22) PCT Filed: Oct. 25, 2012

(86) PCT No.: PCT/IN2012/000703
§ 371 (c)(1),
(2) Date: Apr. 25, 2014

(87) PCT Pub. No.: WO2013/061340
PCT Pub. Date: May 2, 2013

(65) Prior Publication Data
US 2014/0243537 A1 Aug. 28, 2014

(30) Foreign Application Priority Data
Oct. 25, 2011 (IN) .......................... 3039/DEL/2011

(51) Int. Cl.
| | |
|---|---|
| C07D 303/16 | (2006.01) |
| C07D 203/26 | (2006.01) |
| C07D 303/40 | (2006.01) |
| C07F 7/08 | (2006.01) |
| C07C 227/16 | (2006.01) |
| C07C 231/12 | (2006.01) |
| C07C 231/18 | (2006.01) |
| C07C 247/14 | (2006.01) |
| C07F 7/18 | (2006.01) |
| C07C 67/327 | (2006.01) |
| C07D 303/48 | (2006.01) |

(52) U.S. Cl.
CPC ............. *C07C 227/16* (2013.01); *C07C 67/327* (2013.01); *C07C 231/12* (2013.01); *C07C 231/18* (2013.01); *C07C 247/14* (2013.01); *C07D 203/26* (2013.01); *C07D 303/16* (2013.01); *C07D 303/40* (2013.01); *C07D 303/48* (2013.01); *C07F 7/0834* (2013.01); *C07F 7/1856* (2013.01); *C07C 2101/16* (2013.01)

(58) Field of Classification Search
None
See application file for complete search history.

(56) References Cited

U.S. PATENT DOCUMENTS 7,531,687 B2    5/2009   Trussardi

OTHER PUBLICATIONS

Abrecht, Stefan et al., The Synthetic Development of the Anti-Influenza Neuraminidase inhibitor Oseltamivir Phosphate (Tatniflur®): A Challenge for Synthesis & Process Research, Chima, vol. 58, No. 9, 2004, p. 621-629.
Mita, Tsuyoshi et al., Second Generation Catalytic Asymmetric Synthesis of Tamiflu: Allylic Substitution Route, Organic Letters, vol. 9, No. 2, 2007, p. 259-262.
Satoh, Nobuhiro et al., A Practical Syntheis of (−)-Oseltamivir, Agnew. Chem. Int. Ed. 2007, vol. 46, p. 5734-5736.
Trost, Barry, M. et al., A Concise Synthesis of (−)-Oseltamivir, Angew. Chem. Int. Ed. 2008, vol. 47, p. 3759-3761.
D. Grandjean et al.; "Base-Promoted Intramolecular Cyclization of Bromoacetylenic Alcohol Derivatives"; Tetrahedron Letters; vol. 33; No. 34; pp. 4905-4908; 1992.
Frank E. McDonald et al.; "Asymmetric Synthesis of Nucleosides Via Molybdenum-Catalyzed Alkynol Cycloisomerization Coupled with Stereoselective Glycosylations of Deoxyfuranose Glycals and 3-Amidofuranose Glycals"; Journal of the American Chemical Society 1996; 118(28); pp. 6648-6659.
Jonathan D. Moseley et al.; "Influenence of Ester Chain Length, Enyme, and Physical Parameters on Lipase-Catalysed Hydrolyses of Meso-Oxiranedimethanol Esters. Part 2"; Tetrahedron: Asymmetry 11 (2000); pp. 3197-3209.
Patrick Pale et al.; "Silver-Catalyzed Cyclization of Acetylenic Alcohols: Synthesis of Functionalized 2-Methylene-Oxolanes"; European Journal of Organic Chemistry 2000; pp. 1019-1025.
Jingwei Li et al.; "Tandem Enyne Metathesis-Metallotropic [1,3]-Shift for a Concise Total Syntheses of (+)-Asperpentyn, (−)-Harveynone, and (−)-Tricholomenyn A"; American Chemical Society 2009; pp. 571-574.
Varun Rawat et al.; "Synthesis of the Anti-Influenza Agent (−)-Oseltamivir Free Base and (−)-Methyl 3-epi-Shikimate"; Organic & Biomolecular Chemistry 2012; pp. 3988-3990.
Giuliana Righi et al.; "A Study on the Chelation Control in the Regioselective Opening of 2,3-Bifunctionalized Epoxides"; Tetrahedron 57 (2001); pp. 5649-5656.
Ying-Yeung Yeung et al.; "A Short Enantioselective Pathway for the Synthesis of the Anti-Influenza Neuramidase Inhibitor Oseltamivir from 1.3-Butadiene and Acrylic Acid"; Journal of the American Chemical Society 2006; pp. 6310-6311.

*Primary Examiner* — Michael Barker
(74) *Attorney, Agent, or Firm* — Blank Rome LLP

(57) ABSTRACT

The present invention discloses high yielding enantioselective process for synthesis of Oseltamivir from readily available starting material, cis-1,4-butene diol. The process features incorporation of chirality using sharpless asymmetric epoxidation (AE) and diastereoselective Barbier allylation and construction of cyclohexene carboxylic acid ester core through a ring closing metathesis (RCM) reaction. Further also disclosed herein is synthesis of (−)-methyl 3-epi-shikimate.

9 Claims, No Drawings

PROCESS FOR THE PREPARATION OF OSELTAMIVIR AND METHYL 3-EPI-SHIKIMATE

This application is a U.S. national phase application of PCT/IN2012/000703, filed Oct. 25, 2012, which claims the priority of Indian Patent Application No. 3039/DEL/2011, filed Oct. 25, 2011, the disclosures of which are incorporated herein by reference.

FIELD OF THE INVENTION

The present invention relates to a high yielding enantioselective process for synthesis of Oseltamivir from readily available starting material, cis-1,4-butene diol. The process features incorporation of chirality using sharpless asymmetric epoxidation (AE) and diastereoselective Barbier allylation and construction of cyclohexene carboxylic acid ester core through a ring closing metathesis (RCM) reaction. The present invention also relate to synthesis of (−)-methyl 3-epi-shikimate. More particularly, the present invention relates to compounds of general formula 1 and 2.

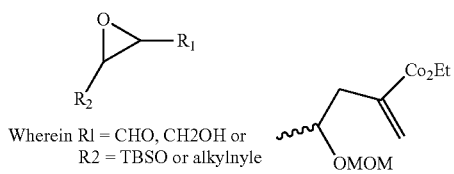

Wherein R1 = CHO, CH2OH or
R2 = TBSO or alkylnyle

Formula 1

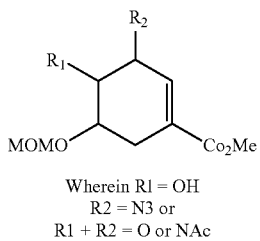

Wherein R1 = OH
R2 = N3 or
R1 + R2 = O or NAc

Formula 2

BACKGROUND OF THE INVENTION

Influenza, commonly referred to as flu, is an infectious disease caused by RNA viruses of the family Orthomyxoviridae (the influenza viruses). Influenza spreads around the world in seasonal epidemics, resulting in the deaths of between 200,000 and 500,000 to people every year, up to millions in some pandemic years. The development of effective antiviral medicines is hampered by the exceptionally high mutation rates of influenza virus. Therefore, in order to be successful, new drugs should target the molecular mechanisms specific to the proliferation of the virus.

Antiviral drug such as Oseltamivir is an orally active neuraminidase inhibitor, which has been widely used for the treatment of H5N1 avian influenza as well as a recent outbreak of H1N1 swine flu. The drug is sold under the trade name Tamiflu, and is taken orally in capsules or as a suspension. It has been used to treat and prevent influenza A virus and influenza B virus infection in over 50 million people since 1999. The anti-influenza drug was initially discovered by Gilead Sciences and subsequently licensed to Roche for production.

The initial synthesis of Tamiflu, developed by Gilead Sciences, employs (−)-quinic acid as the starting material, alternatively, shikimic acid was used for the commercial production. Large quantities of (−)-shikimic acid are obtained by extraction from star anise plant which is grown in China by a biocatalytic process which uses glucose as carbon source. The process is described below in Scheme 1:

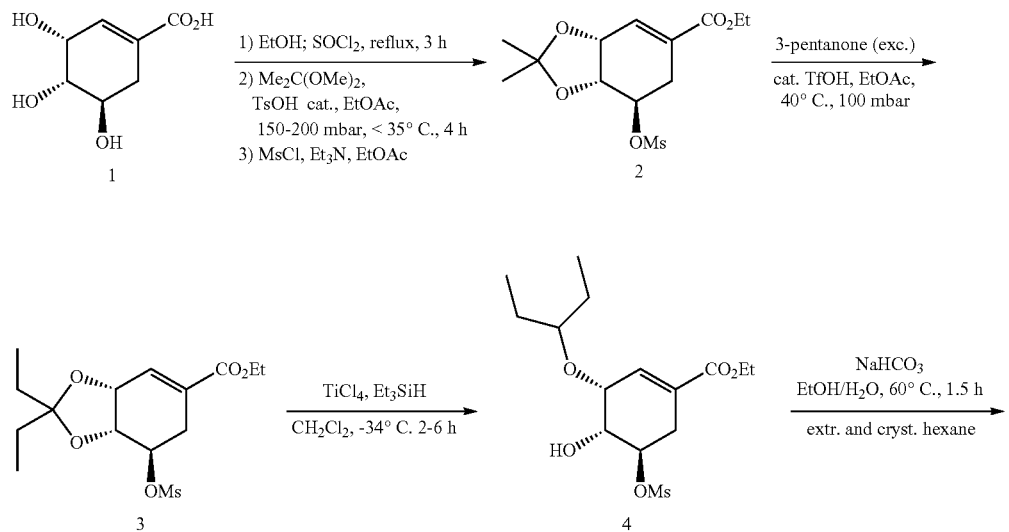

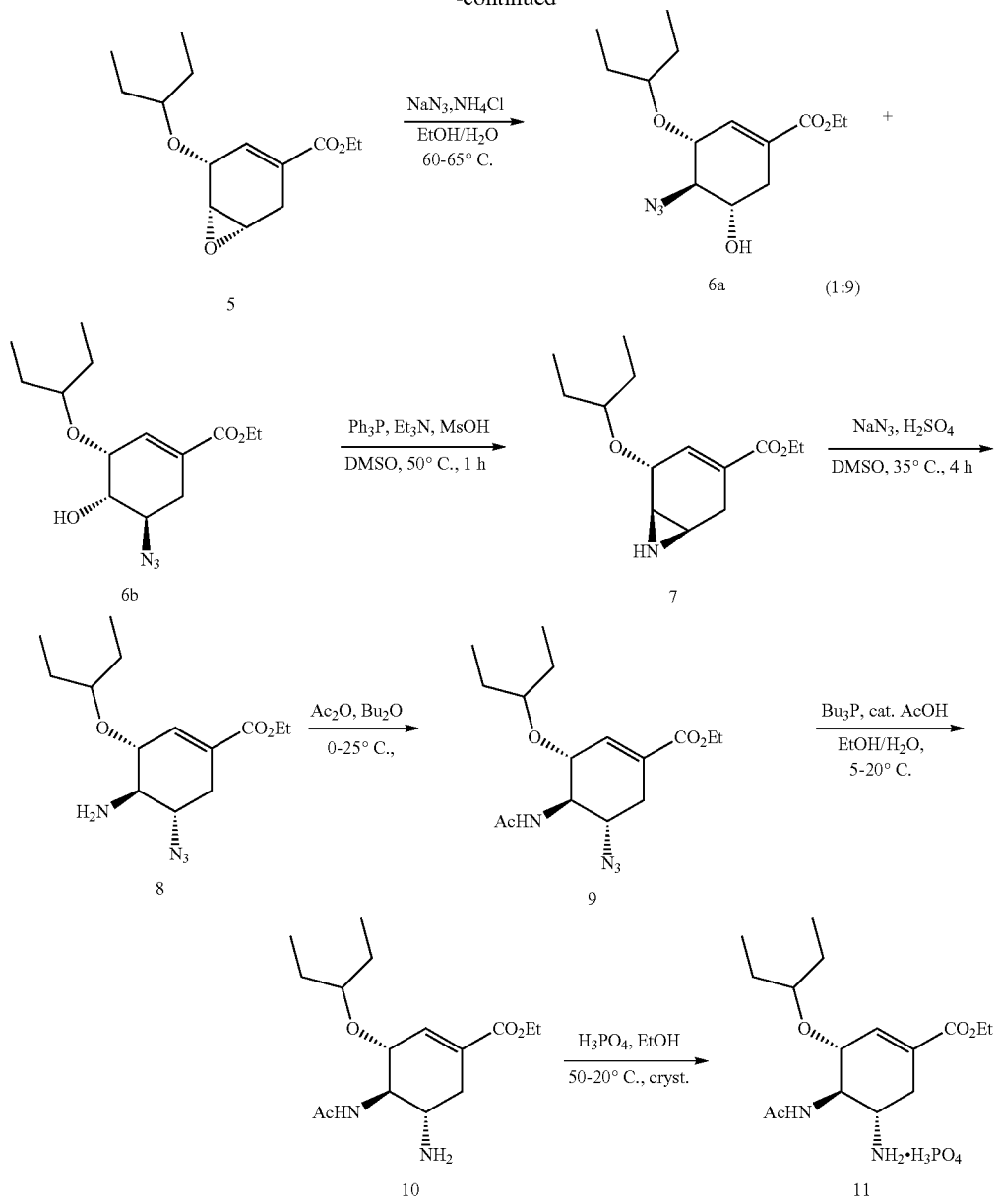
However, the supply of (−)-shikimic acid of consistent purity is problematic due to seasonal and geographical constraints.
U.S. Pat. No. 7,531,687 (Applicant—Roche) relates to a process for the conversion of Shikimic acid to oseltamivir (I), and optionally to an acid addition salt, via the intermediate phosphoramide VII. The process is described in Scheme 2 below:
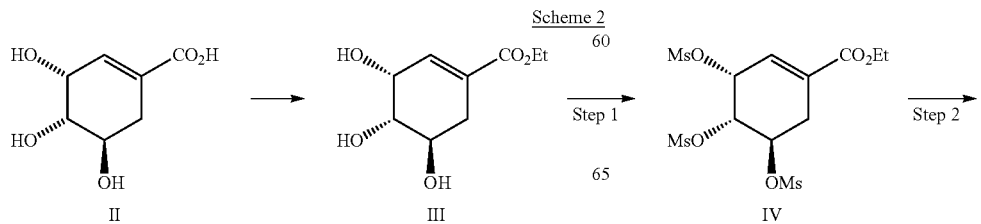

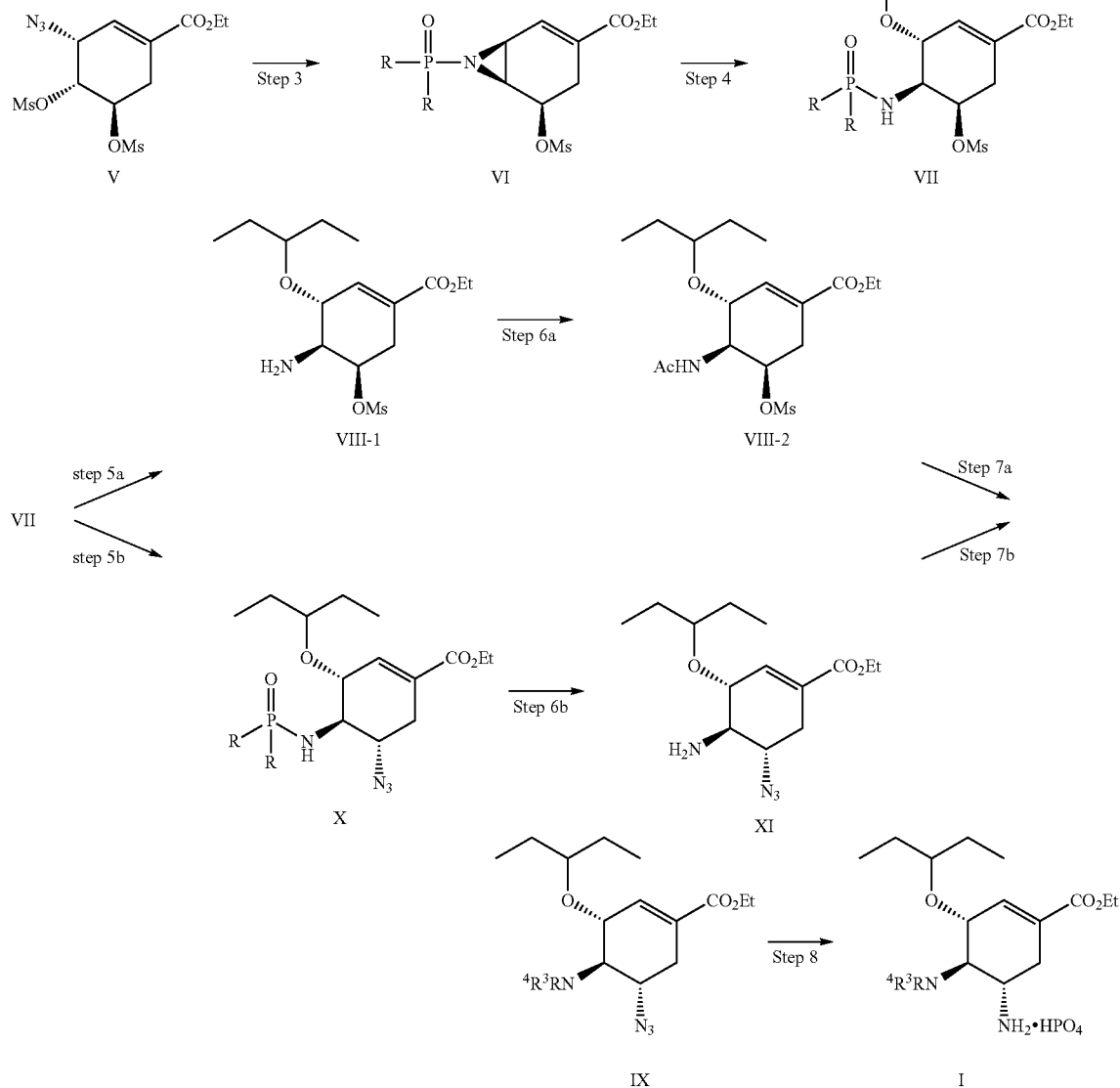

The process comprises the steps of (step 1) converting an alkyl shikimate ester (III) to the corresponding tris-mesylate IV by reacting III with methanesulfonyl chloride the presence of an aprotic organic solvent and an organic base; (step 2) stereoselectively displacing the mesyloxy substituent on C-3 with azide in an organic solvent optionally in the presence of water and a phase transfer catalyst to afford V; (step 3) contacting V with a trialkylphosphite in an inert organic solvent to induce a Staudinger reaction and provide the aziridine (VI); (step 4) opening the aziridine by contacting VI with a Lewis acid in the presence of a first alcohol to form VII; (step 5a) contacting VII with a strong acid in a second alcoholic solvent to hydrolyze of the phosphoramidate and afford the amine VIII-1; (step 6a) contacting VIII-1 with an acylating agent and a base to afford VIII-2; (step 7a) contacting VIII-2 with a azide in a second organic solvent and in the presence of a third alcohol to displace the remaining mesyloxy group to afford IX and (step 8) contacting IX with a reducing agent to afford oseltamivir (I) which is optionally converted to a pharmaceutically acceptable salt.

Article titled "The Synthetic Development of the Anti-Influenza Neuraminidase Inhibitor Oseltamivir Phosphate (Tamiflu®): A Challenge for Synthesis & Process Research" by Karf, Trussadi et. al in CHIMIA International Journal for Chemistry (2004), Volume: 58, Issue: 9, Pages: 621-629 discloses synthesis of Oseltamivir Phosphate from naturally available (−)-shikimic acid as a chiral pool starting material. The process is depicted in Scheme 3 below:

Scheme 3

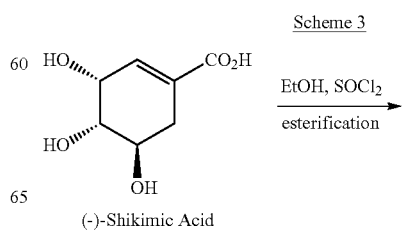

(−)-Shikimic Acid

EtOH, SOCl$_2$
esterification

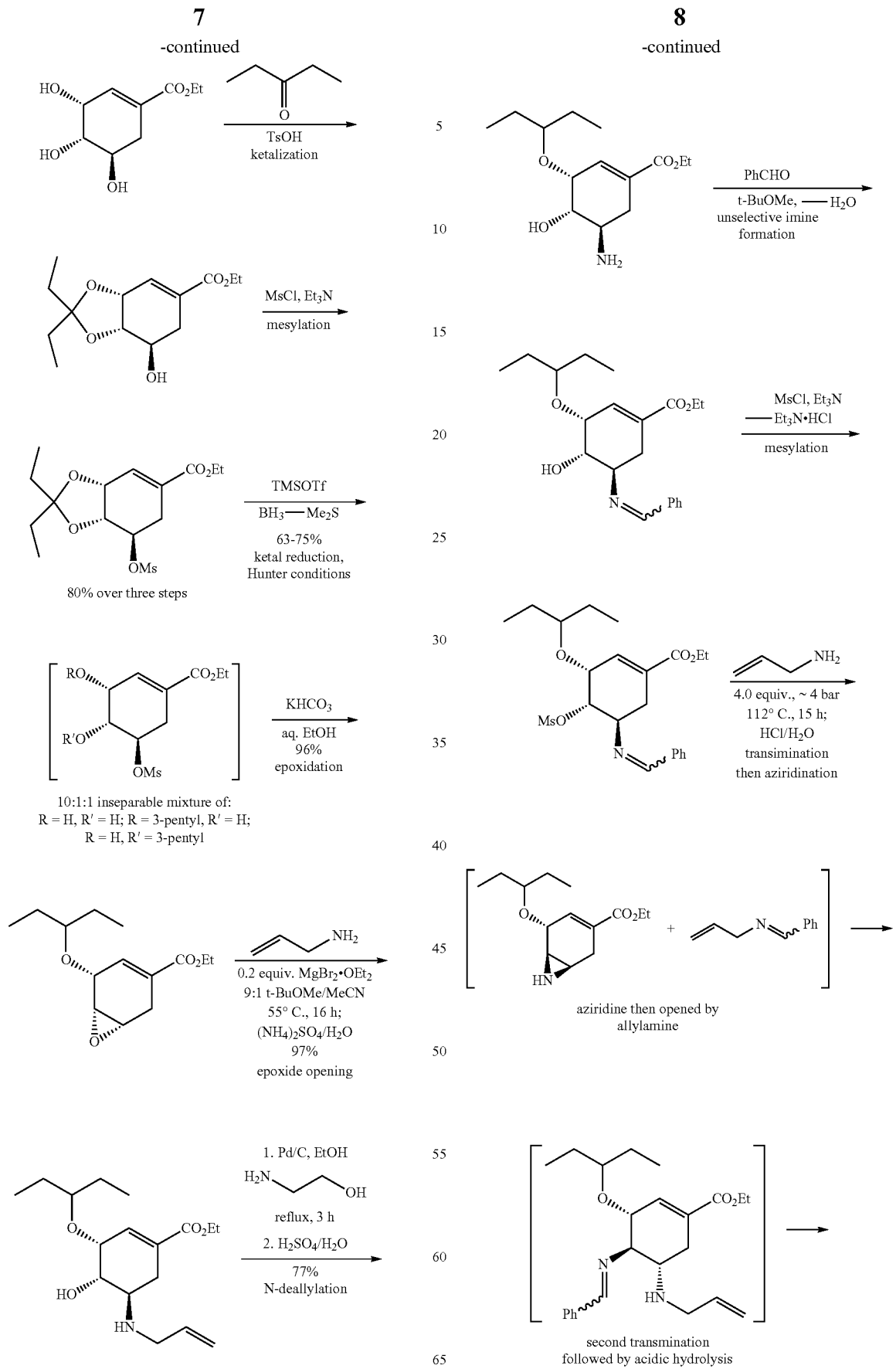

9
-continued

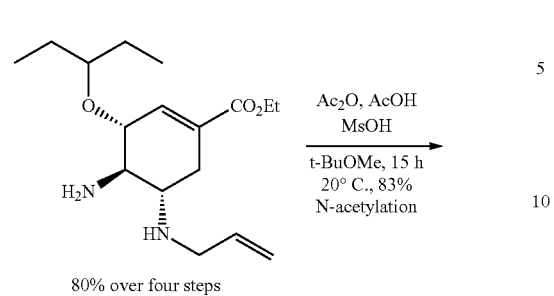

80% over four steps

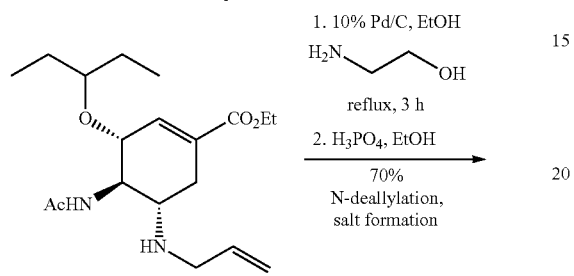

10
-continued

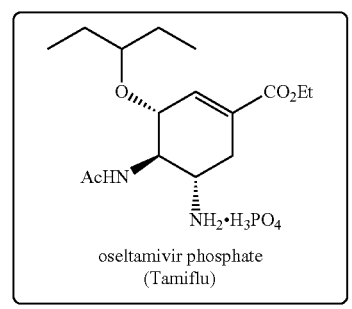

oseltamivir phosphate
(Tamiflu)

An article titled "Short Enantioselective Pathway for the Synthesis of the Anti-Influenza Neuramidase Inhibitor Oseltamivir from 1,3-Butadiene and Acrylic Acid" by E. J. Corey published in J. Am. Chem. Soc., 2006, 128 (19), pp 6310-6311 discloses synthesis of Oseltamivir from 1,3-Butadiene and acrylic Acid as shown in Scheme 4.

Scheme 4

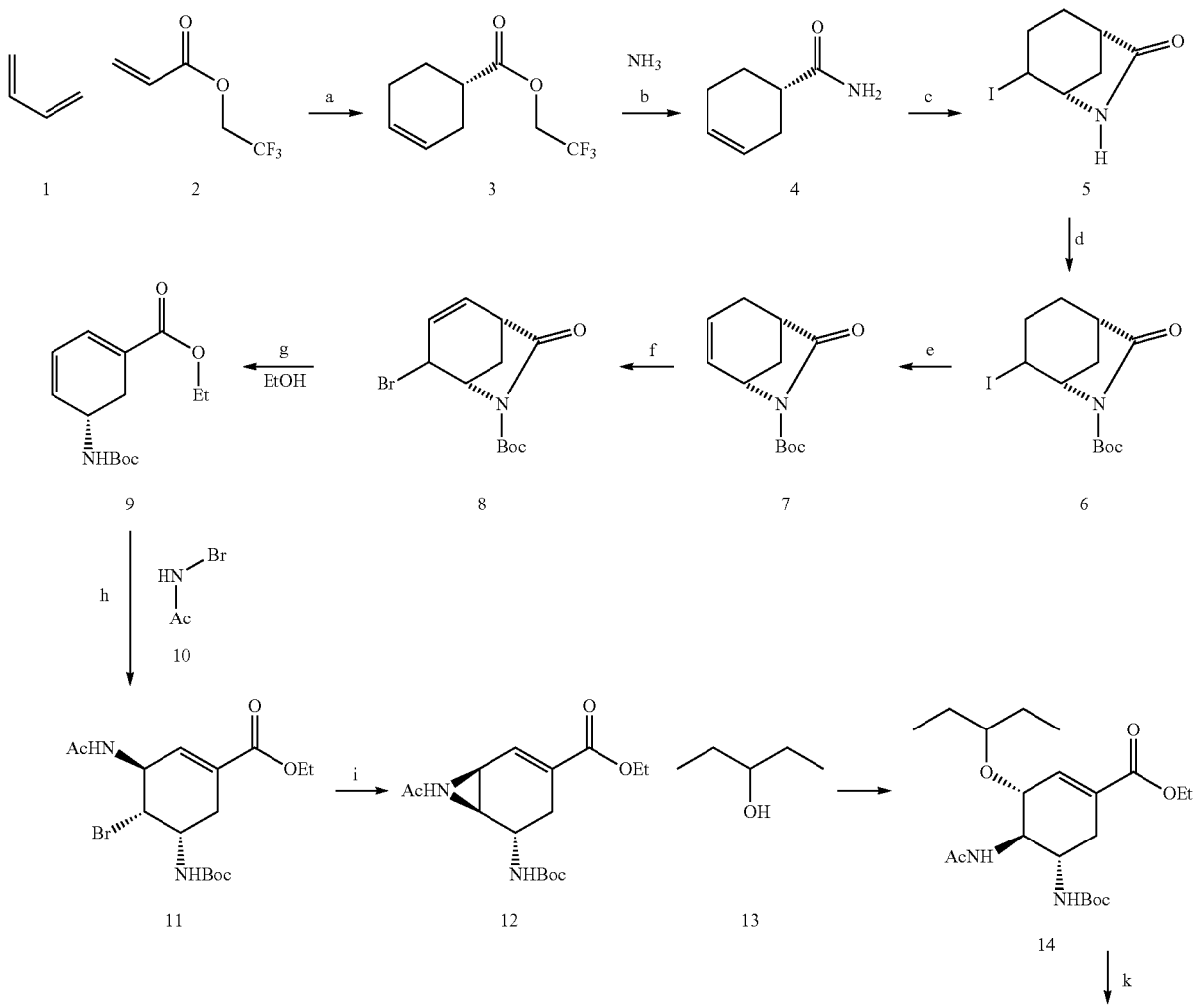

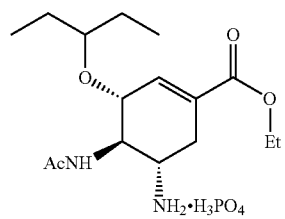

Article titled "Second Generation Catalytic Asymmetric Synthesis of Tamiflu: Allylic Substitution Route" by Masakatsu Shibasaki et. al in Org. Lett., 2007, 9 (2), pp 259-262 discloses Catalytic asymmetric synthesis of Tamiflu. After the catalytic enantioselective desymmetrization of meso-aziridine 3 with TMSN3, using a Y catalyst (1 mol %) derived from ligand 2, an allylic oxygen function and C1 unit on the CC double bond are introduced through cyanophosphorylation of enone and allylic substitution with an oxygen nucleophile (Scheme 5).

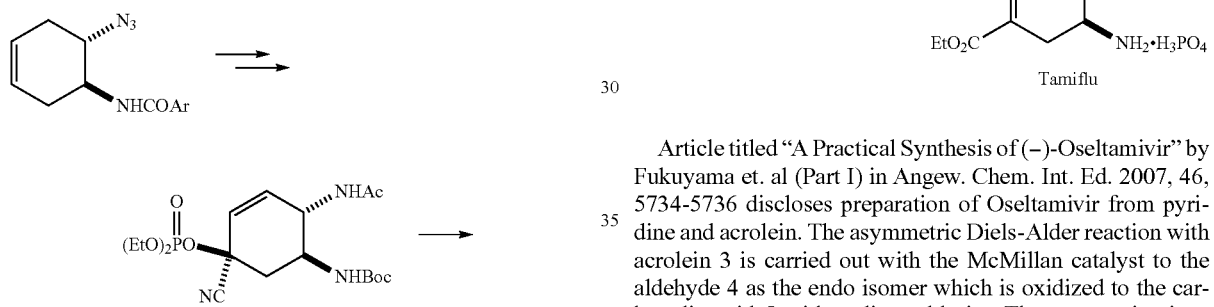

Article titled "A Practical Synthesis of (−)-Oseltamivir" by Fukuyama et. al (Part I) in Angew. Chem. Int. Ed. 2007, 46, 5734-5736 discloses preparation of Oseltamivir from pyridine and acrolein. The asymmetric Diels-Alder reaction with acrolein 3 is carried out with the McMillan catalyst to the aldehyde 4 as the endo isomer which is oxidized to the carboxylic acid 5 with sodium chlorite. The process is given below in Scheme 6

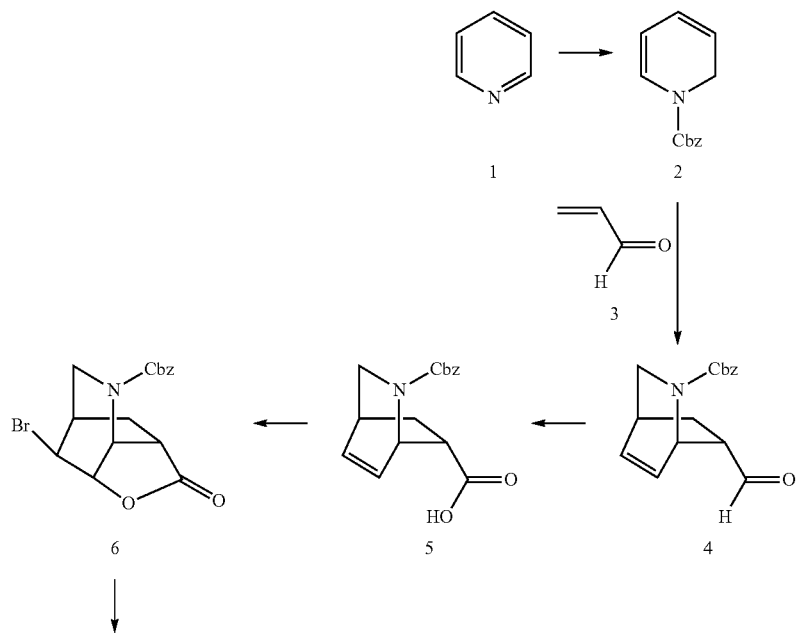

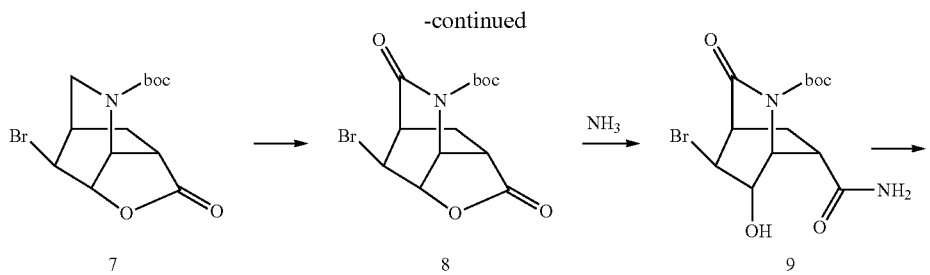

In the article "A Concise Synthesis of (−)-Oseltamivir" by Barry M. Trost, Ting Zhang in Angew. Chem. Int. Ed. 2008, 47, 1-4, synthesis of Oseltamivir is disclosed which is given below in Scheme 7:

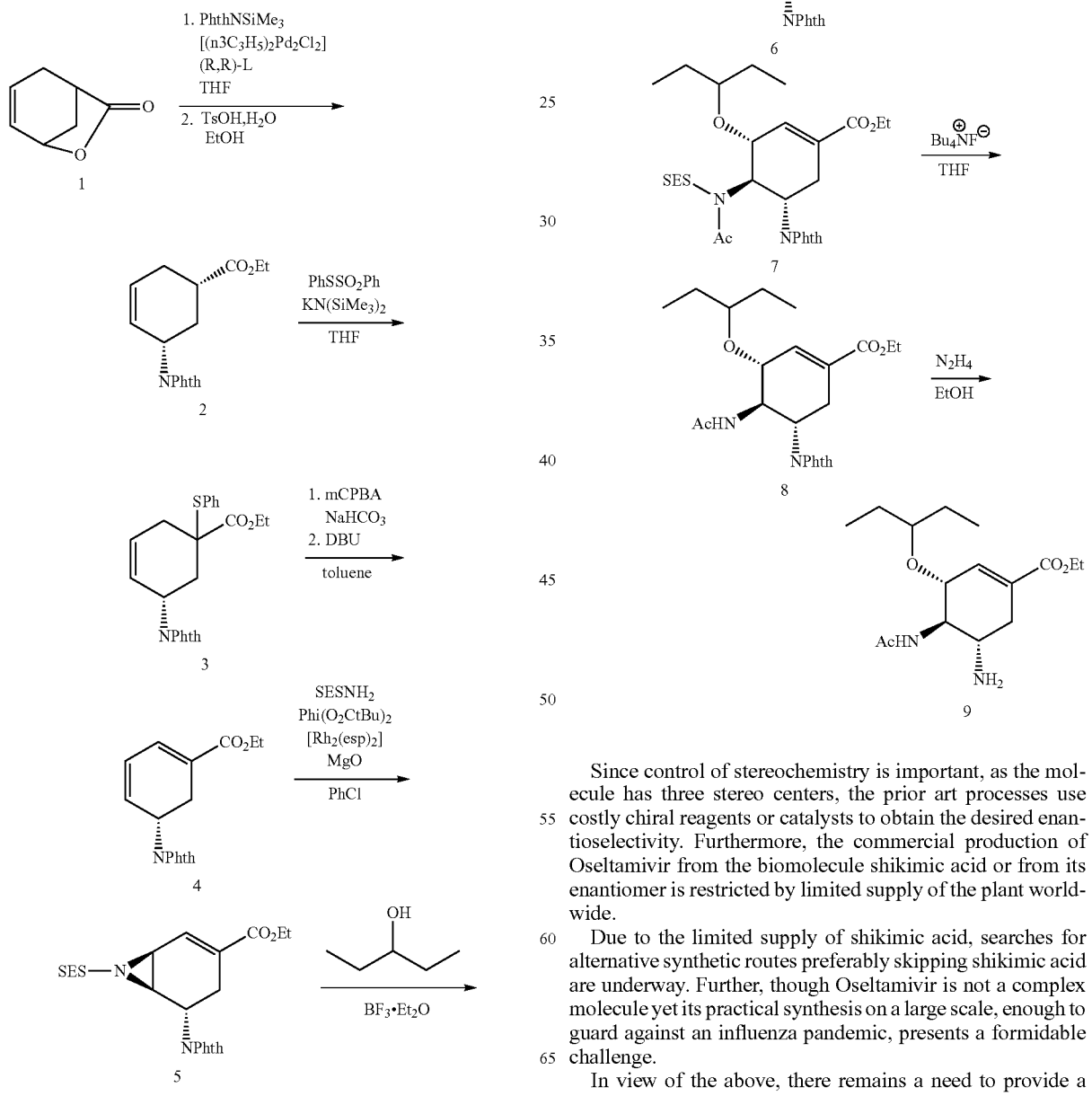

Since control of stereochemistry is important, as the molecule has three stereo centers, the prior art processes use costly chiral reagents or catalysts to obtain the desired enantioselectivity. Furthermore, the commercial production of Oseltamivir from the biomolecule shikimic acid or from its enantiomer is restricted by limited supply of the plant worldwide.

Due to the limited supply of shikimic acid, searches for alternative synthetic routes preferably skipping shikimic acid are underway. Further, though Oseltamivir is not a complex molecule yet its practical synthesis on a large scale, enough to guard against an influenza pandemic, presents a formidable challenge.

In view of the above, there remains a need to provide a high-yielding enantioselective approach towards the synthesis of Anti-Influenza Agent Oseltamivir from readily available and less expensive starting materials.

OBJECTIVE OF THE INVENTION

The main objective of the invention is to provide a high yielding enantioselective process for the synthesis of Anti-influenza Oseltamivir from readily available and less expensive starting material cis-1,4-diol.

Another object of the invention is to provide synthesis of (−)-methyl 3-epi-shikimate, a key intermediate in the process of Oseltamivir.

Another object of the invention is to provide compound of general formula 1 and 2

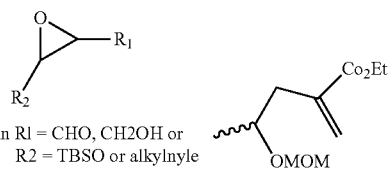

Wherein R1 = CHO, CH2OH or
R2 = TBSO or alkylnyle

Formula 1

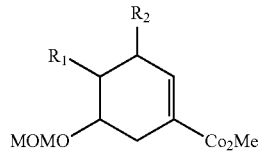

Formula 2

Wherein R1 = OH
R2 = N3 or
R1 + R2 = O or NAc

SUMMARY OF THE INVENTION

Accordingly, the present invention provides a process for the preparation of Oseltamivir with enantioselectivity 98% ee, and methyl 3-epi-shikimate wherein the said process comprises:

(i) monosilylating of cis-1,4-butene diol (6) in a dry aprotic solvent and imidazole and a silyalting agent at the temperature ranging between 0-25 deg C. for a period ranging between 4-8 hours to obtain mono silyl allylic alcohol (Z)-4-(tert-butyldimethylsilyloxy)but-2-en-1-ol (7).

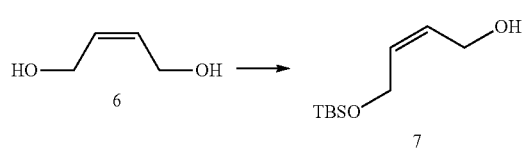 [SMILES: OC/C=C\CO ; CC(C)(C)[Si](C)(C)OC/C=C\CO]

(ii) asymmetric epoxidizing mono silyl allylic alcohol (Z)-4-(tert-butyldimethylsilyloxy)but-2-en-1-ol (7) with Ti(OiPr)4, (+) DET (diethyl tartarate), anhydrous TBHP (tert-butyl hydroperoxide) in a aprotic solvent at a temperature ranging between −10° C. C to −20° C. for a time period of 10 to 20 minutes to obtain epoxy alcohol ((2S,3R)-3-((tert-butyldimethylsilyloxy)methyl)oxiran-2-yl)methanol of formula (8) followed by oxidizing with TEMPO (2,2,6,6-tetramethyl-1-piperidinyloxyl)/BAIB [bis(acetoxy)iodo]benzene] mixture to obtain aldehyde 2R,3R)-3-((tert-butyldimethylsilyloxy)methyl)oxirane-2-carbaldehyde of formula (9);

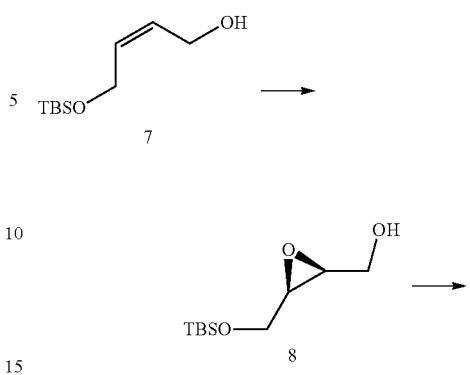

(iii) subjecting aldehyde (9) to diasteroselective Barbier allylation in the presence of ethyl 2-(bromomethyl)acrylate, Zn dust in an aprotic solvent and NH4Cl at the temperature ranging between 25-30° C. for a period of 8-12 hours to obtain the compound 10 ((R)-Ethyl 4-((2S,3R)-3-((tert-butyldimethylsilyloxy)methyl)oxiran-2-yl)-4-hydroxy-2-methylenebutanoate)

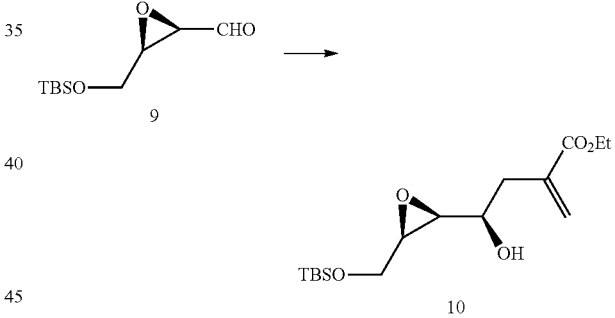

(iv) adding N,N-dipropylethylamine (hunig's base) to a solution of compound 10 as obtained in step (iii) in a dry aprotic solvent in the presence of a protecting agent at a temperature ranging between 0-25° C. for a period of 10-16 hours to obtain compound (R)-ethyl 4-((2S,3R)-3-((tert-butyldimethylsilyloxy)methyl)oxiran-2-yl)-4-(methoxymethoxy)-2-methylenebutanoate of formula 11 followed by desilylation using TBAF (tetrabutyl ammonium fluoride) to obtain compound 12.

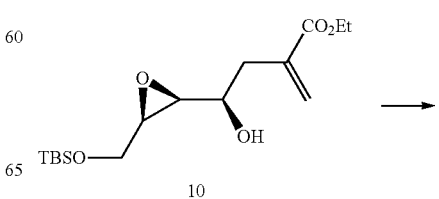

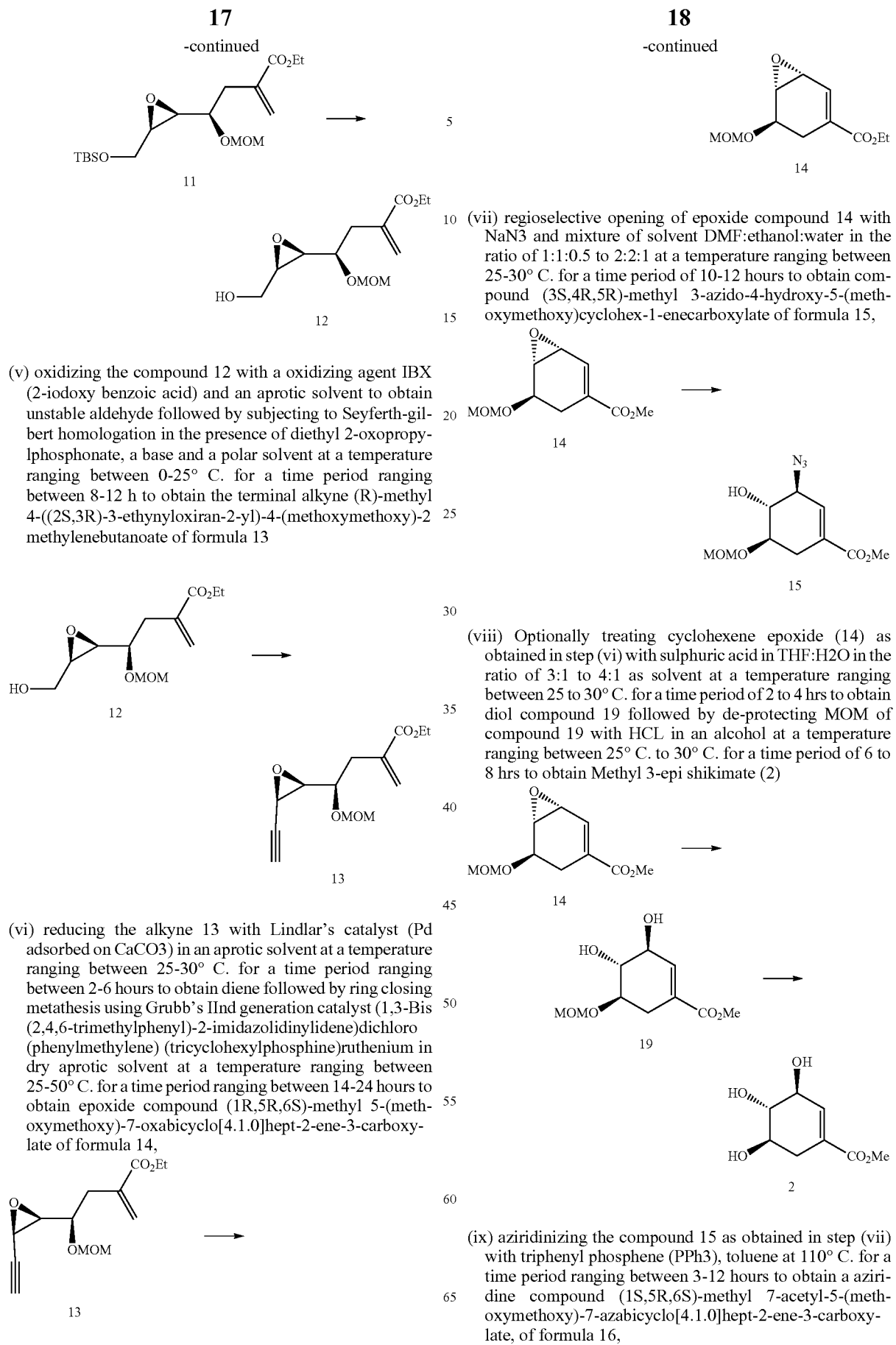

(v) oxidizing the compound 12 with a oxidizing agent IBX (2-iodoxy benzoic acid) and an aprotic solvent to obtain unstable aldehyde followed by subjecting to Seyferth-gilbert homologation in the presence of diethyl 2-oxopropylphosphonate, a base and a polar solvent at a temperature ranging between 0-25° C. for a time period ranging between 8-12 h to obtain the terminal alkyne (R)-methyl 4-((2S,3R)-3-ethynyloxiran-2-yl)-4-(methoxymethoxy)-2 methylenebutanoate of formula 13

(vi) reducing the alkyne 13 with Lindlar's catalyst (Pd adsorbed on CaCO3) in an aprotic solvent at a temperature ranging between 25-30° C. for a time period ranging between 2-6 hours to obtain diene followed by ring closing metathesis using Grubb's IInd generation catalyst (1,3-Bis (2,4,6-trimethylphenyl)-2-imidazolidinylidene)dichloro (phenylmethylene) (tricyclohexylphosphine)ruthenium in dry aprotic solvent at a temperature ranging between 25-50° C. for a time period ranging between 14-24 hours to obtain epoxide compound (1R,5R,6S)-methyl 5-(methoxymethoxy)-7-oxabicyclo[4.1.0]hept-2-ene-3-carboxylate of formula 14, (vii) regioselective opening of epoxide compound 14 with NaN3 and mixture of solvent DMF:ethanol:water in the ratio of 1:1:0.5 to 2:2:1 at a temperature ranging between 25-30° C. for a time period of 10-12 hours to obtain compound (3S,4R,5R)-methyl 3-azido-4-hydroxy-5-(methoxymethoxy)cyclohex-1-enecarboxylate of formula 15, (viii) Optionally treating cyclohexene epoxide (14) as obtained in step (vi) with sulphuric acid in THF:H2O in the ratio of 3:1 to 4:1 as solvent at a temperature ranging between 25 to 30° C. for a time period of 2 to 4 hrs to obtain diol compound 19 followed by de-protecting MOM of compound 19 with HCL in an alcohol at a temperature ranging between 25° C. to 30° C. for a time period of 6 to 8 hrs to obtain Methyl 3-epi shikimate (2)

(ix) aziridinizing the compound 15 as obtained in step (vii) with triphenyl phosphene (PPh3), toluene at 110° C. for a time period ranging between 3-12 hours to obtain a aziridine compound (1S,5R,6S)-methyl 7-acetyl-5-(methoxymethoxy)-7-azabicyclo[4.1.0]hept-2-ene-3-carboxylate, of formula 16,

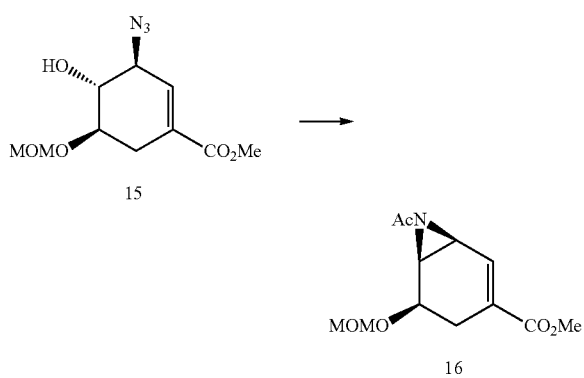

15

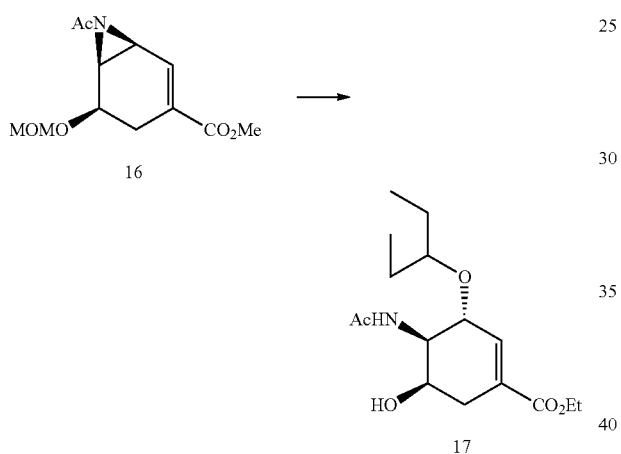

16

(x) regio-selective ring opening of aziridine (16) with pentan-3-ol in the presence of BF3.Et2O at a temperature ranging between 0-25° C. for a time period ranging between 2-12 hours to obtain compound 17 followed by MOM de-protection in an alcohol and HCL at a −10 temperature ranging between 25-30° C. for a time period of 4-12 hours to give compound 17 (3R,4R,5R)-Ethyl 4-acetamido-5-hydroxy-3-(pentan-3-yloxy)cyclohex-1-enecarboxylate

16

17

(xi) Conversion of 17 to oseltamivir by method known in the art.

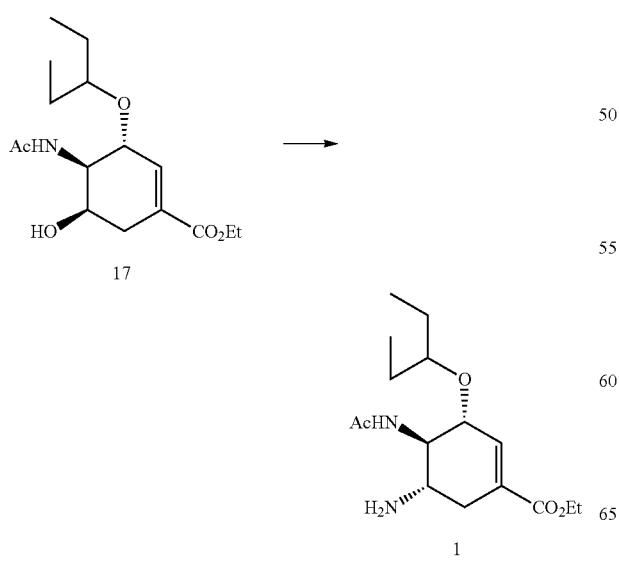

17

1

In one embodiment of the present invention the solvent selected from polar or non-polar solvents; protic or aprotic solvents used is selected from the group comprising of toluene, acetone, ethyl acetate, methanol, THF, DCM, DMSO.

In another embodiment of the present invention the silylating agent used in step 1 (i) is selected from the group comprising of dimethylsilyl (TMS), tert-butyldiphenylsilyl (TBDPS), tert-butyldimethylsilyl (TBS/TBDMS) and triisopropylsilyl (TIPS), [2-(trimethylsilyl)ethoxy]methyl (SEM), tert-butyl dimethylsilyl chloride (TBSCl).

Still in another embodiment of the present invention the base used in step (v) is selected from the group comprising of $K_2CO_3$, $Et_3N$.

Still in another embodiment of the present invention protecting agent used in step (iv) is MOMCl (methyl chloromethyl ether)

Still in another embodiment of the present invention compounds of general formula 1 and 2

Formula 1

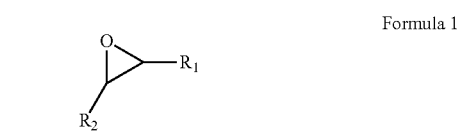

Wherein R1 = CHO, CH2OH or

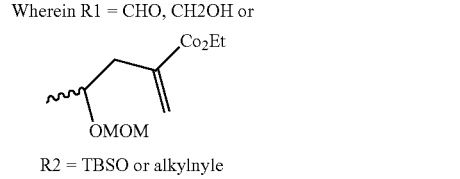

R2 = TBSO or alkylnyle

Formula 2

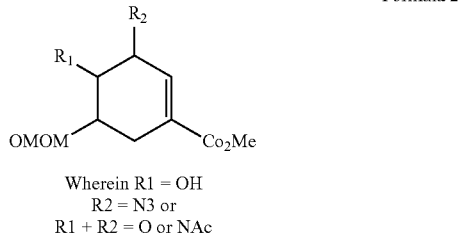

Wherein R1 = OH
R2 = N3 or
R1 + R2 = O or NAc

Still in another embodiment of the present invention compounds of general formula 1 and 2 are represented by the group of the following compounds:

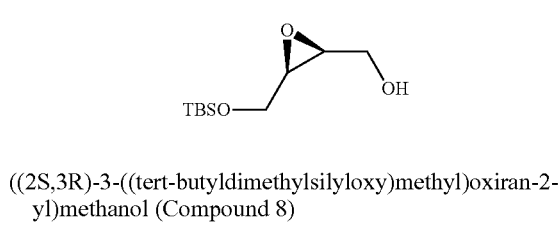

((2S,3R)-3-((tert-butyldimethylsilyloxy)methyl)oxiran-2-yl)methanol (Compound 8)

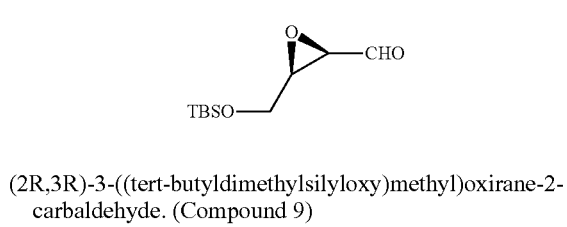

(2R,3R)-3-((tert-butyldimethylsilyloxy)methyl)oxirane-2-carbaldehyde. (Compound 9)

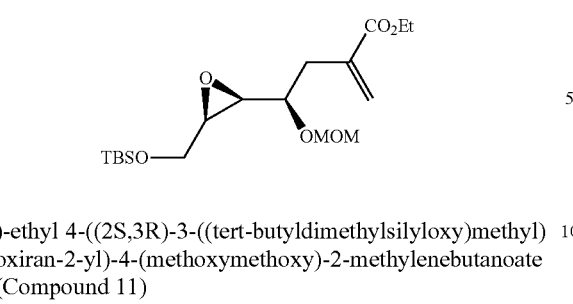

(R)-ethyl 4-((2S,3R)-3-((tert-butyldimethylsilyloxy)methyl)oxiran-2-yl)-4-(methoxymethoxy)-2-methylenebutanoate (Compound 11)

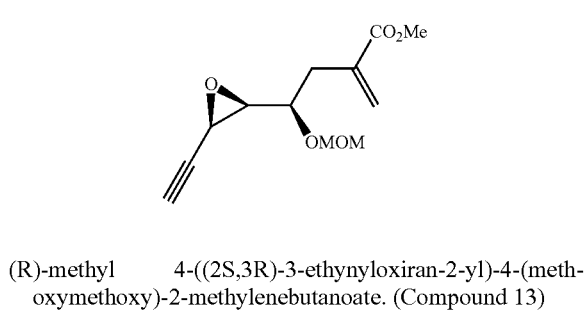

(R)-methyl 4-((2S,3R)-3-ethynyloxiran-2-yl)-4-(methoxymethoxy)-2-methylenebutanoate. (Compound 13)

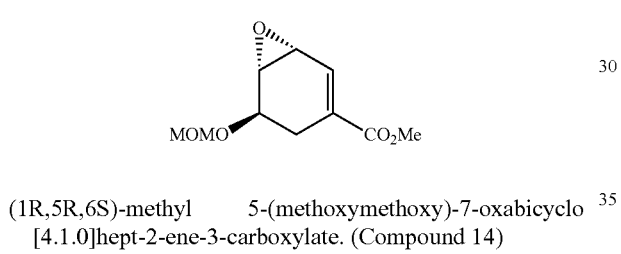

(1R,5R,6S)-methyl 5-(methoxymethoxy)-7-oxabicyclo[4.1.0]hept-2-ene-3-carboxylate. (Compound 14)

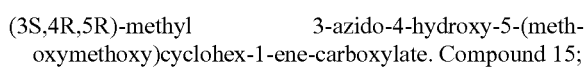

(3S,4R,5R)-methyl 3-azido-4-hydroxy-5-(methoxymethoxy)cyclohex-1-ene-carboxylate. Compound 15;

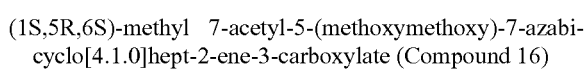

(1S,5R,6S)-methyl 7-acetyl-5-(methoxymethoxy)-7-azabicyclo[4.1.0]hept-2-ene-3-carboxylate (Compound 16)

DETAILED DESCRIPTION OF THE INVENTION

The present invention relates to enantioselective synthesis of Anti-Influenza Agent Oseltamivir (1) and (−)-methyl 3-epi-shikimate (2) from readily available raw material, cis-1,4-butene diol.

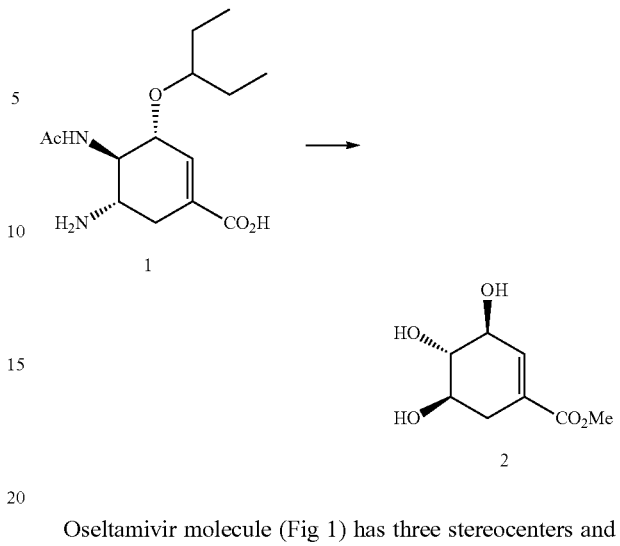

Oseltamivir molecule (Fig 1) has three stereocenters and the sought-after isomer is only 1 of 8 stereoisomers. Hence control of stereochemistry is important during the synthesis of said molecule. The process of the current invention overcomes the shortcomings of processes known in the art by incorporation of chirality using sharpless asymmetric epoxidation (AE) and diastereoselective Barbier allylation. Further, cyclohexene carboxylic acid ester core is constructed through a ring closing metathesis (RCM) reaction. Oseltamivir free base with 98% ee is achieved by the present invention.

The process for preparation of Oseltamivir with enantioselectivity 98% ee, comprises the steps of;

1. Monosilylation of cis-1,4-butene diol (6) to obtain mono-silyl allylic alcohol (7);
2. Asymmetric epoxidation of allylic alcohol (7) with Ti(O-iPr)$_4$, (−)-DET, anhydrous TBHP to give epoxy alcohol (8) followed by oxidation with TEMPO/BAIB mixture to aldehyde (9);
3. Zinc mediated diasteroselective Barbier allylation of aldehyde (9), to syn-epoxy alcohol (10);
4. Selective protection of syn epoxy alcohol (10) with methyl chloromethyl ether (MOMCl) in presence of Hunig's base to give corresponding MOM-ether (11) followed by desilylation of (11) to obtain alcohol (12);
5. Oxidation of (12) with IBX/DMSO mixture to unstable aldehyde, extracting in diethyl ether and subjecting to Seyferth-Gilbert homologation in presence of a base and methanol to afford the terminal alkyne (13) with a completely transesterified methyl ester;
6. Reduction of alkyne (13) with Lindlar's catalyst to corresponding diene followed by ring closing metathesis using Grubb's II$^{nd}$ generation catalyst under high dilution (large excess of solvent, (100 mL) to afford the carbocyclic core in epoxide (14);
7. Regioselective opening of cyclohexene epoxide (14) with NaN$_3$ and NH$_4$Cl to obtain azido alcohol (15);
8. Aziridination of alcohol (15) with Et$_3$N and MsOH followed by acylation to obtain aziridine (16);
9. Regioselective ring opening of aziridine (16) followed by MOM deprotection to give compound 17; and
10. converting 17 to Oseltamivir by method known in the art procedure known in literature X. Lu, F.-F. Wang, N. Quan, X. X. Shi and L.-D. Nie, *Tetrahedron: Asymmetry*, 2011, 22, 1692)

The chirality in the molecule is achieved by subjecting mono silyl protected allylic alcohol (7) to sharpless asymmetric epoxidation with Ti(OiPr)4, (+)-DET (diethyl tartarate), TBHP (tert-butyl hydroperoxide), 4 Angstrom Molecular Seives (A M.S.) at −20° C. to yield epoxy alcohol (8). Alcohol (8) is further oxidized with a oxidizing mixture consisting of TEMPO (2,2,6,6-tetramethyl-1-piperidinyloxyl) and BAIB [bis(acetoxy)iodo]benzene to aldehyde (9). Zinc-mediated aqueous Barbier allylation of (9) with ethyl 2-(bromomethyl) acrylate in polar aprotic solvent in aq. sat. NH4Cl forms corresponding homoallylic alcohols (10) in good yields (84%, for both diastereomers) and with good diastereoselectivity (10:1).). The syn-epoxy alcohol (10) was confirmed by its correlation data (NOESY and COSY).

In the process of the present invention, ring closing metathesis has been used for the facile construction of cyclohexene carboxylic acid ester core. This is realized by subjecting the diene obtained by reduction of alkyne (13) to Grubb's II$^{nd}$ generation catalyst (under high dilution condition) large excess of solvent) to cyclohexene epoxide (14).

In the process, the solvents include polar or non-polar solvents; protic or aprotic solvents and are selected from toluene, dichloromethane (DCM), acetone, ethyl acetate, methanol, THF, DCM, DMSO etc.

Cis-1,4-butene diol (6) is mono protected with silyl group selected from trimethylsilyl (TMS), tert-butyldiphenylsilyl (TBDPS), tert-butyldimethylsilyl (TBS/TBDMS) and triisopropylsilyl (TIPS), [2-(trimethylsilyl)ethoxy]methyl (SEM), tert-butyl dimethylsilyl chloride (TBSCl) in a solvent to obtain corresponding mono silyl protected allylic alcohol (7). The mono silyl protected allylic alcohol (7) is subjected to Sharpless asymmetric epoxidation with Ti(OiPr)$_4$, (+)-DET (diethyl tartrate), TBHP (tert-butyl hydroperoxide), 4 A M.S. at −20° C. to yield epoxy alcohol (8).

Compound (8) is oxidized with a oxidizing mixture consisting of TEMPO (2,2,6,6-tetramethyl-1-piperidinyloxyl) and BAIB [bis(acetoxy)iodo]benzene in dry $CH_2Cl_2$ to aldehyde (9). Zinc mediated Barbier allylation of aldehyde (9) is effected with ethyl 2-(bromomethyl) acrylate in polar aprotic solvent in aq. sat. $NH_4Cl$ to obtain corresponding homoallylic alcohols (10). Preferably, syn-epoxy alcohol (10) is obtained and its formation is confirmed by its correlation data (NOESY and COSY). Compound (10) is further treated with Methyl chloromethyl ether (MOMCl) in presence of Hunigs base (N,N diisopropylethylamine) to give corresponding ether (11) followed by desilylation with TBAF (tetrabutyl ammonium fluoride) in presence of THF to give alcohol (12). The free hydroxy group in (12) is oxidized with IBX (2-iodoxy benzoic acid) in dry DMSO at 25 deg C. giving the corresponding aldehyde, which is found to be unstable during silica gel purification. The aldehyde is extracted in a solvent and immediately (without purification) is subjected to Seyferth-Gilbert homologation using dimethyl-(1-diazo-2-oxopropyl)phosphonate (Bestman-Ohira reagent) in presence of an inorganic base such as $K_2CO_3$ in MeOH to obtain terminal alkyne (13). Subsequent reduction of alkyne (13) with Lindlar's catalyst (Pd adsorbed on CaCO3) in presence of MeOH, gave the corresponding diene, which is further subjected to ring closing metathesis using Grubb's II$^{nd}$ generation catalyst (1,3-Bis(2,4,6-trimethylphenyl)-2 imidazolidinylene) dichloro(phenylmethylene)(tricyclohexylphosphine)ruthenium (under high dilution condition) to carbocyclic core (14). The regioselective opening of epoxide (14) with $NaN_3$ and $NH_4Cl$ in a mixture of DMF:EtOH:H2O (2:2:1) gives azido alcohol (15). Aziridine formation from azido alcohol (15) is facilitated by treating compound (15) with $PPh_3$ in MsOH and in presence of a base such as $Et_3N$ and a solvent THF followed by acylation with acylating agent in presence of a base $Et_3N$ to give aziridine (16). Aziridine (16) is reacted with pentan-3-ol in presence of 1.5 equiv. of $BF_3OEt_2$ followed by MOM deprotection with 2N HCl in MeOH to give 17 which is converted to the Oseltamivir by known literature methods.

The above described process for the preparation of Oseltamivir is schematically given below in Scheme 8.

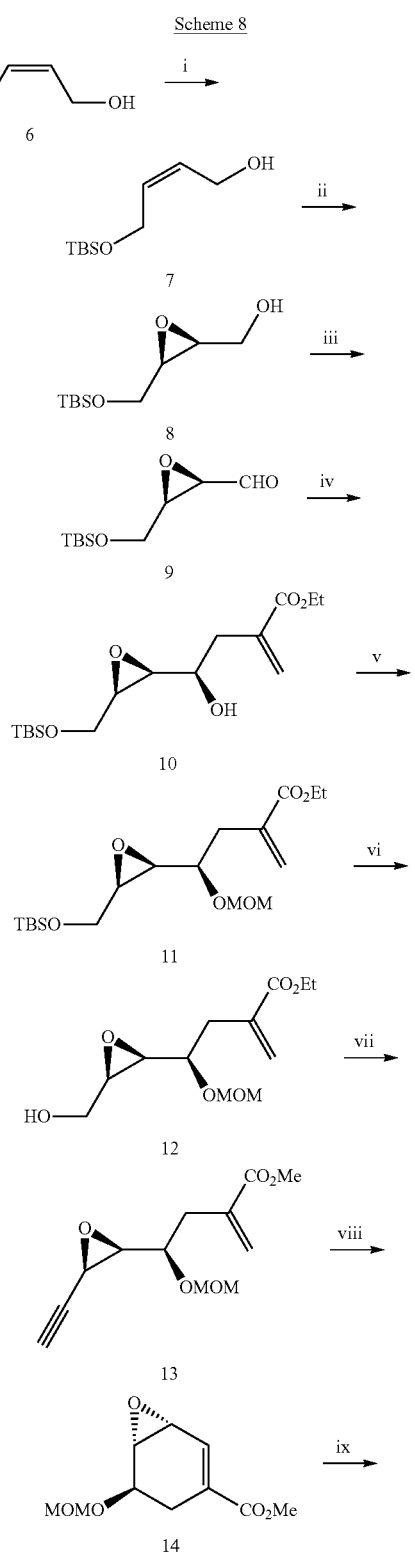

Scheme 8

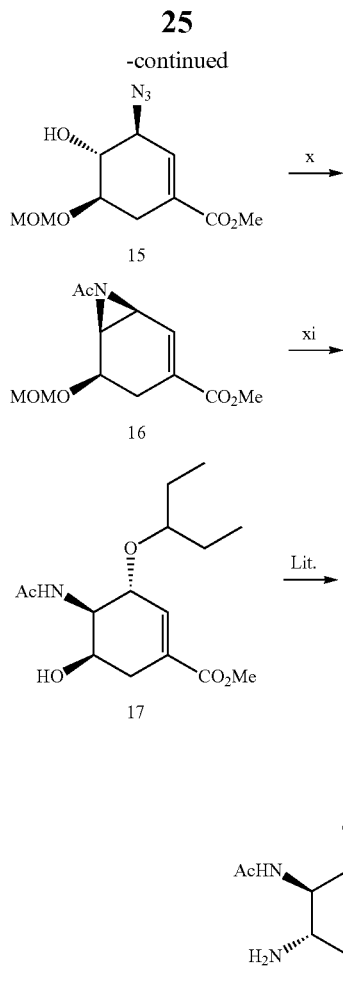

Reagents and conditions: (i) TBSCl, imid., dry CH$_2$Cl$_2$, 0-25° C., 8 h, 73%; (ii) Ti(OiPr)$_4$, (+)-DET, TBHP, 4° A M.S., -10° C., 12 h, 93%; (iii) Tempo, BAIB, dry CH$_2$Cl$_2$, 25° C. 1 h, 95%; (iv) Zn dust, ethyl 2-(bromomethyl)acrylate, THF, aq. sat. NH$_4$Cl, 25° C., 10 h, 64%; (v) MOMCl, Hunigs base, dry CH$_2$Cl$_2$, 0-25° C., 10 h, 90%; (vi) TBAF, THF, 0-25° C., 2 h, 88%; (vii) (a) IBX, dry DMSO, 25° C., 2 h; (b) diethyl 2-oxopropylphosphonate, K$_2$CO$_3$, MeOH 82% (for two steps); (viii) (a) Lindlars cat., ETHYL/PYIRIDINE/1-OCTENE, MeOH, 25° C., 6 h; (b) Grubbs II, dry CH$_2$Cl$_2$, 50° C., 12 h, 85% (for two steps); (ix) NaN$_3$, DMF:EtOH:H2O (2:2:1), 25° C., 10 h, 83%; (x) PPh$_3$, toluene, reflux, 3 h; (c) Ac2O, Et$_3$N, EtOAc, 25° C., 2 h, 81% (for two steps); (xi) (a) 3-pentanol, BF$_3$OEt$_2$, 0° C., 2 h; (xii) (b) HCl, EtOH, 25° C., 4 h, 64% (for two steps).

The present invention disclose a novel intermediate of formula (8); ((2S,3R)-3-((tert-butyldimethylsilyloxy)methypoxiran-2-yl)methanol.

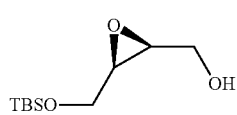 [SMILES: CC(C)(C)[Si](C)(C)OC[C@H]1O[C@H]1CO]

The intermediate (9); (2R,3R)-3-((tert-butyldimethylsilyloxy)methyl)oxirane-2-carbaldehyde.

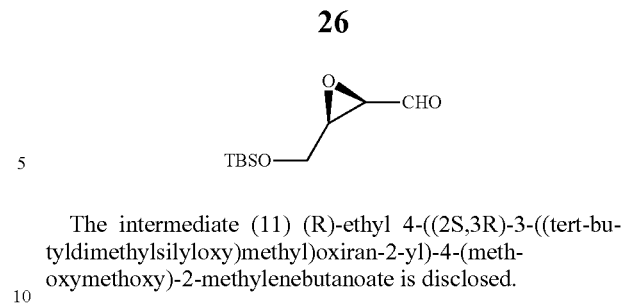

The intermediate (11) (R)-ethyl 4-((2S,3R)-3-((tert-butyldimethylsilyloxy)methyl)oxiran-2-yl)-4-(methoxymethoxy)-2-methylenebutanoate is disclosed.

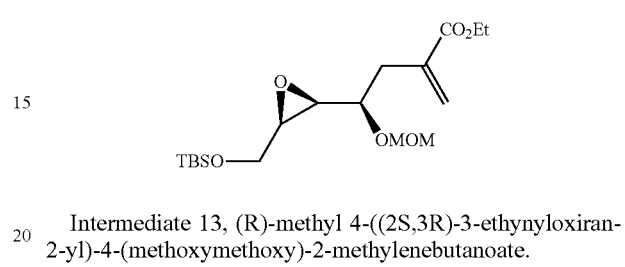

Intermediate 13, (R)-methyl 4-((2S,3R)-3-ethynyloxiran-2-yl)-4-(methoxymethoxy)-2-methylenebutanoate.

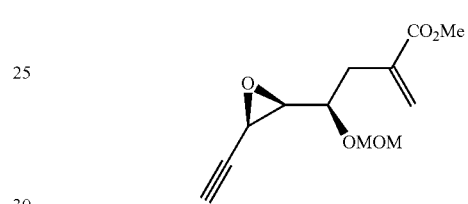

The novel intermediate, (14) (1R,5R,6S)-methyl 5-(methoxymethoxy)-7-oxabicyclo[4.1.0]hept-2-ene-3-carboxylate.

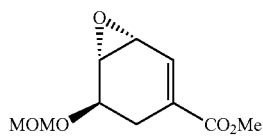

A novel intermediate (15), (3S,4R,5R)-methyl 3-azido-4-hydroxy-5-(methoxymethoxy)cyclohex-1-ene-carboxylate.

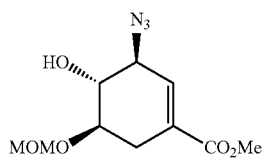

In another embodiment, an intermediate (16) (1S,5R,6S)-methyl 7-acetyl-5-(methoxymethoxy)-7-azabicyclo[4.1.0]hept-2-ene-3-carboxylate, is provided.

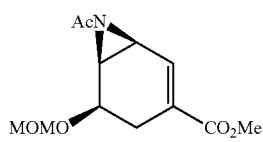

The present invention discloses synthesis of Methyl 3-epi shikimate (2) from the cyclohexene epoxide precursor (14). Compound (14) is derived from cis-1,4 butene diol (6) by the aforementioned process steps. Accordingly, conversion of epoxide (14) to triol of formula (2) comprises ring opening of epoxide (14) with sulphuric acid in THF:H2O (5:1) as solvent mixture, to obtain the corresponding diol-19; followed by MOM deprotection in compound 19 with 2N HCl in methanol.

The synthesis of 3-epimer of (–)-methyl shikimate (2) is given below in Scheme 9.

Scheme 9

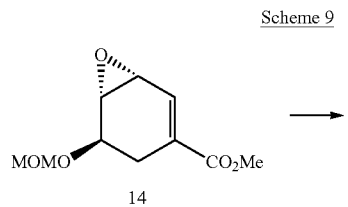

Based on retrosynthesis analysis, the present inventors concluded that cyclohexene epoxide (14) can be considered as key precursor in the synthesis of oseltamavir (1) and (–)-methyl 3-epi-shikimate (2).

The stereochemistry of the cyclohexene epoxide derivative (14) is confirmed by its conversion to a literature known compound (2) given above. Correlation with literature values, confirms the relative as well as absolute stereochemistry of the functionalized carbocyclic core.

The present invention discloses synthesis of oseltamivir with high enantioselectivity from the novel intermediate cyclohexene epoxide (14), which process comprises the following steps;

1. Regioselective opening of cyclohexene epoxide (14) with NaN$_3$ and NH$_4$Cl to obtain azido alcohol (15);
2. Aziridination of alcohol (15) with Ph3P in refluxing toluene followed by acylation to obtain aziridine (16);
3. Regioselective ring opening of aziridine (16) with pentan-3-ol followed by MOM deprotection to give compound 17; and
4. Conversion of 17 to Oseltamivir by method known in the art.

Scheme 10

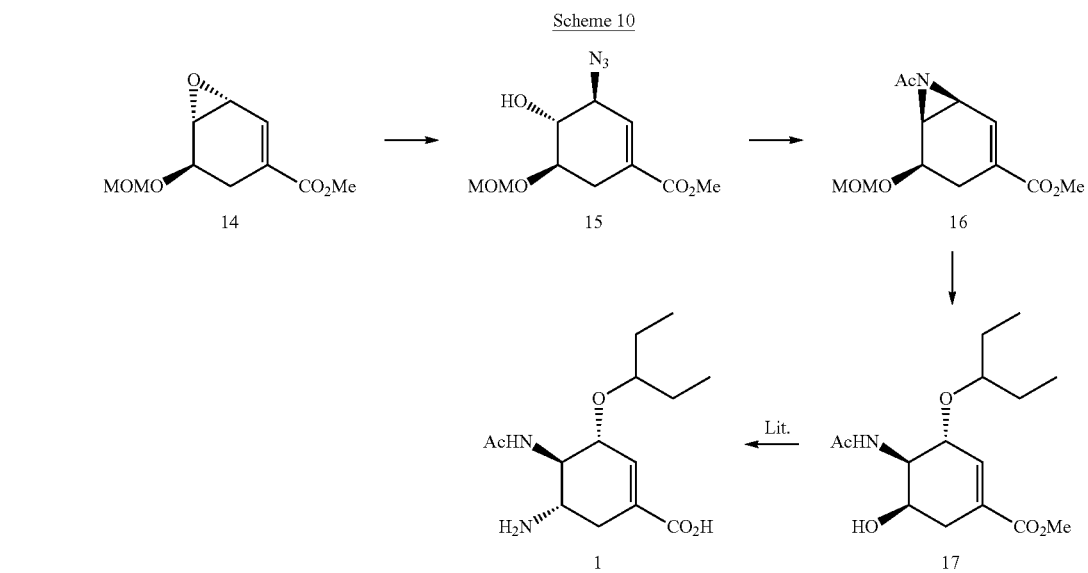

(i) NaN$_3$, DMF:EtOH:H2O (2:2:1), 25° C., 12 h, 83%; (ii) PPh$_3$, toluene, reflux, 3 h; (iii) Ac2O, Et$_3$N, EtOAc, 25° C., 2 h, 81% (for two steps); (iv) 3-pentanol, BF$_3$OEt$_2$, 0° C., 2 h; (v) HCl, EtOH, 25° C., 4 h, 64% (for two steps).

The present invention relates to the use of the compound Oseltamivir prepared by the instant process for the treatment or prevention of influenza.

The invention relates to the use of the compound for the preparation of a medicament for the treatment or prevention of influenza.

The compound of the present invention is suitably formulated into pharmaceutical compositions for administration to human subjects in a biologically compatible form suitable for administration in vivo. The present invention provides a pharmaceutical composition comprising the compound of the instant invention either alone or as its salts along with suitable pharmaceutically acceptable excipients such as carrier, diluent, binder, lubricant etc.

In conclusion, the present invention provides a novel enantioselective synthetic route towards (–)-Methyl 3-epi-shiki-

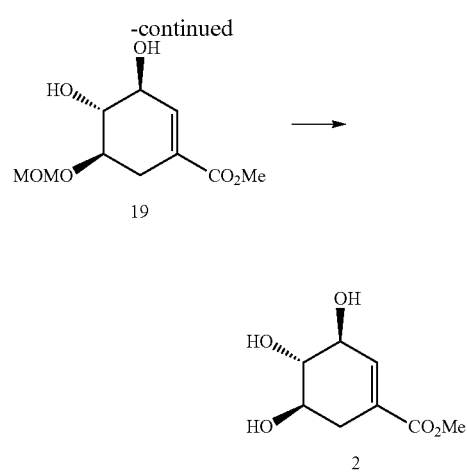

Reagents and conditions: (i) H2SO4, THF:H2O, 25° C., 2 h, 96%; (ii) HCl, MeOH, 25° C., 4 h, 74%.

mate and Anti-Influenza Agent Oseltamivir incorporating a successful application of Sharpless asymmetric epoxidation (AE) and diastereoselective Barbier allylation. Ring closing metathesis (RCM) has been used for the facile construction of cyclohexene carboxylic acid ester core. Throughout the synthesis, operationally simple reactions with high overall yields requiring a relatively low amount of inexpensive and non-toxic reagents are used which make the present approach an attractive and useful process.

GENERAL INFORMATION

Solvents were purified and dried by standard procedures before use. Optical rotations were measured using sodium D line on a JASCO-181 digital polarimeter. $^1$H NMR and $^{13}$C NMR spectra were recorded on Brucker AC-200 spectrometer unless mentioned otherwise. Elemental analysis was carried out on a Carlo Erba CHNS-O analyzer. IR spectra were recorded on a Perkin-Elmer model 683 B and absorption is expressed in cm$^{-1}$. Purification was done using column chromatography (230-400 mesh).

The present invention is illustrated herein below with examples, which are illustrative only and should not be construed to limit the scope of the present invention in any manner.

Example 1

(Z)-4-(tert-butyldimethylsilyloxy)but-2-en-1-ol, (7)

To a solution of cis-1,4-butene diol (6) (20.0 g, 227.27 mmol) in dry CH$_2$Cl$_2$ (700 mL) at 0° C. was added imidazole (23.21 g, 340.91 mmol) and tert-butyldimethylsilyl chloride (37.68 g, 250.0 mmol). The reaction mixture was stirred at 0° C. for 6 h. After completion of reaction (monitored by TLC), it was diluted with CH$_2$Cl$_2$ (500 mL) washed with water, brine and dried over anhydrous Na$_2$SO$_4$. Removal of solvent under reduced pressure gave the crude product which was then purified by column chromatography with petroleum ether/EtOAc (9:1 v/v) to give (7) as a colorless liquid.

Yield: 73%; colorless liquid; IR (CHCl$_3$): 777, 837, 1033, 1088, 1255, 1471, 2857, 2929, 3354 cm$^{-1}$; $^1$H NMR (200 MHz, CDCl$_3$): δ 0.04 (s, 6H), 0.86 (s, 9H), 2.2 (brs, 1H), 4.17-4.26 (m, 4H), 5.57-5.61 (m, 2H); $^{13}$C NMR (50 MHz, CDCl$_3$): 6-5.3, 18.3, 25.9, 58.6, 59.5, 130.1, 131.1; Anal. Calcd for C$_{10}$H$_{22}$O$_2$Si requires C, 59.35; H, 10.96. Found: C, 59.38; H, 10.99%.

Example 2

((2S,3R)-3-((tert-butyldimethylsilyloxy)methyl)oxiran-2-yl)methanol, [(−)-8]

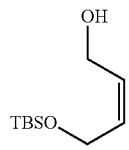

To a stirred suspension of powdered 4 Å molecular sieves (10.0 g) in dry CH$_2$Cl$_2$ (700 mL), titanium tetraisopropoxide (5.6 g, 20 mol %) was added under nitrogen atmosphere. The reaction mixture was cooled to −10° C. and (+)diethyl tartrate (4.4 g, 30 mol %) added and stirred for 10 min. To the above solution, tert-butyl hydroperoxide 5-6 molar solution in decane (35.2 mL, 2 equiv.) was added and stirred at −10° C. for further 30 min, after which allylic alcohol 7 (20 g, 98.83 mmol) dissolved in dry CH$_2$Cl$_2$ (150 mL) was added and stirred at −10° C. for 12 h. After completion of the reaction (monitored by TLC), the reaction mixture was quenched with 1M NaOH (25 mL) with further stirring for 1 h at −10° C. The organic layer was then separated, washed with brine solution, dried over anhyd. Na$_2$SO$_4$ and concentrated under reduced pressure. The crude compound was purified by column chromatography using petroleum ether/ethyl acetate (8:2 v/v) to afford the epoxy alcohol (−)-8 as a colorless liquid.

Yield: 93%; colorless liquid; [α]$_D^{25}$ −11.1 (c 2.0, CHCl3) IR (CHCl3): 777, 837, 1047, 1257, 1472, 2858, 2955, 3441 cm$^{-1}$; $^1$H NMR (200 MHz, CDCl$_3$): δ 0.04 (s, 6H), 0.86 (s, 9H), 2.9 (brs, 1H), 3.13-3.20 (m, 2H), 3.65-3.73 (m, 4H); $^{13}$C NMR (50 MHz, CDCl$_3$): δ −5.3, −5.4, 18.6, 25.8, 56.2, 56.5, 60.6, 61.6; Anal. Calcd for C10H22O3Si requires C, 55.00; H, 10.15. Found: C, 55.07; H, 10.18%.

Example 3

(2R,3R)-3-((tert-butyldimethylsilyloxy)methyl)oxirane-2-carbaldehyde, [(+)-9]

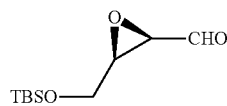 [SMILES: CC(C)(C)[Si](C)(C)OC[C@H]1O[C@H]1C=O]

To a solution of epoxy alcohol (+)-8 (15.0 g) in dry CH$_2$Cl$_2$ was added in one portion bis-acetoxy iodobenzene (24.34, 75.6 mmol) and TEMPO (1.07 g, 6.9 mmol). The reaction mixture was then allowed to stir at 25° C. for 1 h. After completion of reaction (monitored by TLC), the reaction mixture was quenched by addition of saturated solution of aq. ammonium thiosulphate (log in 100 mL water). The organic layer was separated, washed with brine and subjected to column chromatographic purification with petroleum ether/ethyl acetate (9:1 v/v) to afford the epoxy aldehyde (+)-9.

Yield: 95%; yellow liquid; [α]D25 +43.0 (c 3.0, CHCl3). IR (CHCl3): 778, 838, 1099, 1256, 1472, 1720, 2858, 2930 cm$^{-1}$; $^1$H NMR (200 MHz, CDCl$_3$): δ 0.08 (s, 6H), 0.89 (s, 9H), 3.34-3.44 (m, 2H), 3.90-4.09 (m, 2H), 9.47 (d, J=4.2 Hz, 1H); $^{13}$C NMR (50 MHz, CDCl3): δ −5.5, 18.2, 25.7, 57.4, 59.8, 60.1, 197.4; Anal. Calcd. for C10H20O3Si requires C, 55.52; H, 9.32. Found: C, 55.60; H, 9.43%.

Example 4

(R)-ethyl 4-((2S,3R)-3-((tert-butyldimethylsilyloxy) methyl)oxiran-2-yl)-4-hydroxy-2-methylenebutanoate, (10)

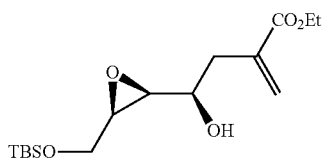 [SMILES: C=C(C[C@@H](O)[C@@H]1O[C@@H]1CO[Si](C)(C)C(C)(C)C)C(=O)OCC]

To a pre-cooled (0° C.), well stirred mixture of (+)-9 (4 g, 18.51 mmol), Zn dust (3 g, 45 mmol) and ethyl 2-(bromoester)acrylate (8 g, 41 mmol) in 80 mL of THF was added a saturated solution of NH$_4$Cl (8 mL). The mixture was stirred for 10 h at ambient temperature 25° C. until the aldehyde was totally consumed (monitored by TLC). The mixture was filtered and the precipitate was thoroughly washed with THF (3×10 mL). THF was then removed under vacuum and the remaining solution extracted with EtOAc (100 mL). The organic layer was washed with brine and dried over anhydrous Na$_2$SO$_4$. Removal of solvent under reduced pressure gave crude product which on chromatographic separation with petroleum ether/ethyl acetate (8:2 v/v) gave title compound syn-epoxy alcohol 10 along with minor amount of its corresponding diastereomer as a yellow colored liquid in 4:1 ratio.

Yield: 64%; yellow liquid; $[\alpha]_D^{25}$ −19.2 (c 2.0, CHCl$_3$); 98% ee HPLC analysis: Column: Chiracel OJ-H (4.6×250 nm), mobile phase: hexane/isopropyl alcohol (90/10), flow rate: 0.5 mL/min, retention time: 15.747 min (+)-isomer, 17.517 min (−)-isomer; IR (CHCl$_3$): 778, 838, 1097, 1256, 1472, 1715, 2857, 2956, 3471 cm$^{-1}$; $^1$H NMR (200 MHz, CDCl$_3$): δ 0.10 (d, J=3.3 Hz, 6H), 0.91 (s, 9H), 1.32 (t, J=7.0 Hz, 3H), 2.58 (dd, J=7.8, 14.1 Hz, 1H), 2.74 (dd, J=3.8, 14.1 Hz, 1H), 2.91 (m, 1H), 3.12 (m, 1H), 3.18 (brs, 1H), 3.61 (m, 1H), 3.78 (dd, J=5.8, 11.8 Hz, 1H), 3.90 (dd, J=5.8, 11.5 Hz, 1H), 4.24 (q, J=7.3, 14.3 Hz, 2H), 5.76 (s, 1H), 6.29 (s, 1H); $^{13}$C NMR (50 MHz, CDCl$_3$): 8-5.4, −5.3, 14.1, 18.2, 25.8, 37.8, 56.1, 58.2, 60.9, 61.9, 69.0, 127.9, 136.5, 167.6; Anal. Calcd for C$_{16}$H$_{30}$O$_5$Si: C, 58.15; H, 9.15. Found: C, 58.20; H, 9.12%.

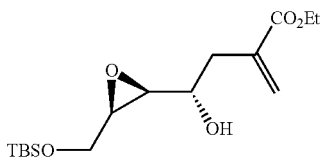 [SMILES: C=C(C[C@H](O)[C@@H]1O[C@@H]1CO[Si](C)(C)C(C)(C)C)C(=O)OCC]

Yield: 16%; yellow liquid; $^1$H NMR (200 MHz, CDCl$_3$): δ 0.08 (d, J=3.0 Hz, 6H), 0.90 (s, 9H), 1.32 (t, J=7.2 Hz, 3H), 2.54-2.60 (m, 2H), 2.99 (dd, J=4.2, 7.3 Hz, 1H), 3.14 (dd, J=4.7, 10.5 Hz, 1H), 3.68-3.81 (m, 2H), 4.20 (q, J=7.1, 14.3 Hz, 2H), 5.72 (s, 1H), 6.27 (s, 1H); $^{13}$C NMR (50 MHz, CDCl$_3$): δ −5.3, −5.2, 14.2, 18.3, 25.9, 37.1, 57.7, 59.8, 60.9, 61.7, 68.7, 128.1, 136.2, 166.9.

Example 5

(R)-ethyl 4-((2S,3R)-3-((tert-butyldimethylsilyloxy)methyl)oxiran-2-yl)-4-(methoxymethoxy)-2-methylenebutanoate, (11)

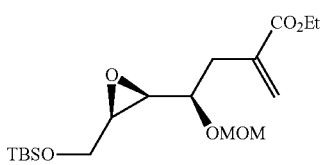

To a solution of compound 10 (3 g, 9.9 mmol) in dry CH$_2$Cl$_2$ (50 mL) was added DIPEA (Hunig's base) 1.3 g, 29.7 mmol), followed by addition of MOMCl (1 mL, 19.8 mmol) at 0° C. The mixture was stirred for 10 h and H$_2$O (10 mL) was added to quench the reaction. The aqueous layer was extracted with CH$_2$Cl$_2$ (30 mL×3). The combined organic layers were washed with brine (20 mL) and dried over Na$_2$SO$_4$. After evaporation of the solvent, the residue was purified by chromatography (petroleum ether/ethyl acetate=9/1) to give MOM protected compound 11 as a colorless oil.

Yield: 90%; colorless liquid; $[\alpha]_D^{25}$ +2.9 (c 1.0, CHCl$_3$); IR (CHCl3): 778, 838, 1150, 1257, 1716, 2857, 2955 cm$^{-1}$; $^1$H NMR (200 MHz, CDCl3): δ 0.08 (d, J=2.9 Hz, 6H), 0.90 (s, 9H), 1.31 (t, J=7.1 Hz, 3H), 2.53-2.57 (m, 2H), 2.96-3.09 (m, 2H), 3.32 (s, 3H), 3.62-3.87 (m, 3H), 4.16 (q, J=7.2, 14.4 Hz, 2H), 4.56 (dd, J=6.7 Hz, 1H), 4.84 (dd, J=6.8 Hz, 1H), 5.68 (s, 1H), 6.25 (s, 1H); $^{13}$C NMR (50 MHz, CDCl3): δ −5.4, −5.2, 14.2, 18.3, 25.9, 35.4, 55.5, 55.6, 59.1, 60.7, 61.8, 73.3, 95.3, 127.7, 136.2, 166.4; Anal. Calcd for C18H34O6Si: C, 57.72; H, 9.15. Found: C, 57.78; H, 9.12%.

Example 6

(R)-ethyl 4-((2S,3R)-3-(hydroxymethyl)oxiran-2-yl)-4-(methoxymethoxy)-2-methylenebutanoate, (12)

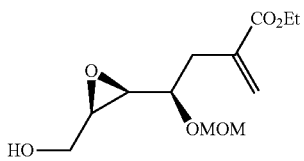

To a well stirred solution of silyl ether 11 (1.1 g, 2.94 mmol) was added 1 M solution of tetrabutylammonium fluoride (6.2 mL, 5.87 mmol) at 0° C. The reaction mixture was stirred at this temperature for 2 h after which the solvent was removed under reduced pressure and the residue was subjected to column chromatography with petroleum ether/ethyl acetate (5:5 v/v) to afford free alcohol 12 oily liquid.

Yield: 88%; colorless liquid; $[\alpha]_D^{25}$ +4.1 (c 0.6, CHCl$_3$); IR (CHCl$_3$, cm$^{-1}$): 919, 1048, 1305, 1410, 1632, 1716, 2983.3, 3453; $^1$H NMR (200 MHz, CDCl$_3$): 1.22 (t, J=7.1 Hz, 3H), 2.44 (dd, J=9.0, 14.0 Hz, 1H), 2.68 (dd, J=3.4, 13.6 Hz, 1H), 2.83 (m, 1H), 3.09 (m, 1H), 3.24 (brs, 1H), 3.30 (s, 3H), 3.55 (m, 2H), 3.79 (m, 1H), 4.11 (q, J=7.1, 13.3 Hz, 2H), 4.52 (d, J=7.2 Hz, 1H), 4.66 (d, J=7.2 Hz, 1H), 5.59 (s, 1H), 6.16 (s, 1H); $^{13}$C NMR (50 MHz, CDCl$_3$): δ 14.2, 36.5, 55.4, 56.1, 57.8, 59.9, 60.7, 72.6, 96.0, 127.7, 136.4, 166.7; Anal. Calcd for C$_{12}$H$_{20}$O$_6$ requires C, 55.37; H, 7.74. Found: C, 55.43; H, 7.90%.

Example 7

(R)-methyl 4-((2S,3R)-3-ethynyloxiran-2-yl)-4-(methoxymethoxy)-2-methylenebutanoate, (13)

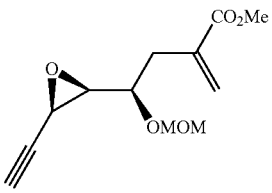

To a solution of epoxy alcohol 12 (1.4 g, 4 mmol) in DMSO (5 mL) in a round-bottomed flask was added IBX (1.68 g, 6 mmol) in one portion and the reaction mixture was stirred for 1 h at ambient temperature (25° C.). The reaction mixture was quenched with diethylether (5 mL), H$_2$O (0.5 mL) and filtered through a pad of celite. The residue was repeatedly washed with diethyl ether (50 mL). The filtrate was washed with H$_2$O, brine, dried (Na$_2$SO$_4$) and concentrated to give the crude aldehyde, which was pure enough and used in the next step without further purification. To a solution of crude aldehyde and K₂CO₃ (900 mg, 8 mmol) in 20 mL dry MeOH and diethyl-1-diazo-2-oxopropylphosphonate (1.26 g, 6 mmol) were added under continuous stirring till completion of the reaction was indicated by TLC (2 h) (25° C.). The reaction mixture was diluted with diethylether (100 mL), washed with aq. solution of NaHCO₃ and dried over Na₂SO₄. Evaporation of solvent yielded analytically pure terminal alkyne 13

Yield: 82%; colorless liquid; $[\alpha]_D^{25}$ −9.4 (c 0.5, CHCl₃); IR (CHCl₃, cm⁻¹): 818, 1149, 1304, 1441, 1514, 1632, 1721, 2116, 2924; ¹H NMR (200 MHz, CDCl₃): 2.45 (d, J=1.6 Hz, 1H), 2.61 (dd, J=7.4, 14.3 Hz, 1H), 2.79 (dd, J=5.4, 15.3 Hz, 1H), 2.98 (dd, J=3.7, 8.1 Hz, 1H), 3.34 (s, 3H), 3.48-3.51 (m, 1H), (3.77 (s, 3H), 3.80 (m, 1H), 4.63 (d, J=6.7 Hz, 1H), 4.71 (d, J=6.8 Hz, 1H), 5.72 (d, J=1.0 Hz, 1H), 6.27 (d, J=1.3 Hz, 1H); ¹³C NMR (50 MHz, CDCl₃): δ 35.4, 45.2, 51.8, 55.7, 58.5, 73.6, 75.1, 78.2, 95.7, 127.7, 136.2, 167.4; Anal. Calcd for C₁₂H₁₆O₅ requires C, 59.99; H, 6.71; O, 33.30. Found: C, 60.02; H, 6.78%.

Example 8

(1R,5R,6S)-methyl 5-(methoxymethoxy)-7-oxabicyclo[4.1.0]hept-2-ene-3-carboxylate, (14)

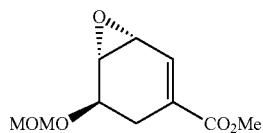

To a solution of 13 (240 mg, 1 mmol) in 5 mL of ethyl acetate/pyridine/1-octene (10:1:1) was added Lindlar's catalyst (12.0 mg). The reaction mixture was stirred for 6 h under a balloon of H₂ at room temperature and filtered through a celite pad. The filtrate was concentrated and the residue was purified by silica gel column chromatography using petroleum ether/ethyl acetate (7:3 v/v) as eluent to give diene A mixture of diene (400 mg, 1.65 mmol) and Grubbs' second-generation catalyst (70 mg, 5 mol %) in dry CH2Cl2 (50 mL) was stirred under reflux for 14 h. The reaction mixture was evaporated and then purified on silica gel chromatography by eluting with petroleum ether/ethyl acetate (7:3 v/v) to afford 14 (0.16 g, 82%) as gum.

Yield: 90%; thick liquid; $[\alpha]D25$−32.7 (c 0.5, CHCl₃); IR (CHCl₃, cm⁻¹): 1091, 1139, 1235, 1387, 1497, 1579, 1719, 2986; ¹H NMR (200 MHz, CDCl₃): 2.13-2.28 (m, 1H), 2.83 (m, 1H), 3.45 (s, 3H), 3.47 (m, 1H), 3.66 (m, 1H), 3.76 (s, 3H), 4.03 (m, 1H), 4.79 (s, 2H), 6.99 (t, J=3.4 Hz, 1H); 13C NMR (50 MHz, CDCl₃): δ 26.5, 46.5, 51.9, 55.0, 55.4, 69.3, 95.9, 128.3, 131.1, 167.5; Anal. Calcd for C10H14O5 requires C, 56.07; H, 6.59. Found: C, 56.01; H, 6.53%.

Example 9

(3S,4R,5R)-methyl 3-azido-4-hydroxy-5-(methoxymethoxy)cyclohex-1-enecarboxylate (15)

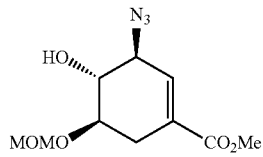

To a solution of cyclic epoxy ester 14 (107 mg, 0.5 mmol) in DMF/EtOH/H2O (1:1:0.5 mL) were added NH4Cl (160.5 g, 3 mmol) and NaN3 (197.4 g, 3 mmol) at 0° C. The mixture was then stirred at 25° C. for 10 h. After completion of reaction (monitored by TLC), EtOH was removed by rotary evaporation. The remaining solution was extracted with EtOAc (100 mL×3). The combined organic layers were washed with, brine (20 mL×6) and dried (Na2SO4). After evaporation of the solvent, the residue was purified by chromatography (petroleum ether/ethyl acetate (7/3 v/v) to obtain compound 15.

Yield: 83%; yellow liquid; [α]D25+17.3 (c 0.7, CHCl3); IR (CHCl3, cm⁻¹): 1073, 1176, 1235, 1365, 1448, 1489, 1561, 1714, 2106, 2994, 3345; ¹H NMR (200 MHz, CDCl₃): 2.17-2.34 (m, 1H), 2.89-3.00 (m, 1H), 3.45 (s, 3H), 3.63-3.67 (m, 2H), 3.77 (s, 3H), 4.10 (m, 1H), 4.77 (s, 2H), 6.59 (t, J=2.5 Hz, 1H); 13C NMR (50 MHz, CDCl3): δ 30.5, 52.1, 55.8, 63.3, 74.5, 77.8, 96.7, 129.8, 134.3, 165.7; Anal. Calcd for C10H15N3O5 requires C, 46.69; H, 5.88; N, 16.33. Found: C, 46.61; H, 5.85; N, 16.38%.

Example 10

(1S,5R,6S)-methyl 7-acetyl-5-(methoxymethoxy)-7-azabicyclo[4.1.0]hept-2-ene-3-carboxylate, (16)

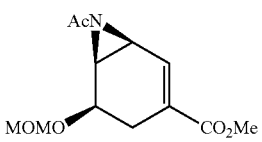

To a solution of azido alcohol 15 (150 mg, 0.58 mmol) in toluene (5 mL) was added triphenylphosphine (152 mg, 0.58 mmol) and the reaction mixture was refluxed for 3 h at 110° C. After removal of the solvent under reduced pressure, diethylether (1 mL) was added, and the mixture cooled with ice-bath. The precipitated triphenylphosphine oxide was removed by filtration and the filtrate evaporated. This procedure was repeated to remove any traces of triphenylphosphine oxide. The residue obtained was then dissolved in dry CH₂Cl₂ (20 mL) cooled at 0° C. To this solution was added Et₃N (175.74 mg, 1.74 mmol), DMAP (4-Dimethylamine pyridine) (5 mg) and acetic anhydride (118.32 mg, 1.16 mmol) and the mixture stirred at 25° C. for further 45 minutes. After completion of reaction (monitored by TLC), the reaction mixture was quenched by addition of H₂O (10 mL). The organic layer was separated, washed with brine, dried (Na₂SO₄) and subjected to column chromatographic purification with petroleum ether/ethyl acetate (7:3 v/v) to afford the cyclic acetamide aziridine 16.

Yield: 81%; colorless liquid; [α]D25 −57.8 (c 0.5, CHCl3); IR (CHCl3, cm⁻¹): 1073, 1195, 1255, 1324, 1369, 1448, 1708, 1732, 2987, 3115; ¹H NMR (200 MHz, CDCl3): 2.10 (s, 3H), 2.20-2.27 (m, 1H), 2.86-2.96 (m, 2H), 3.16 (m, 1H), 3.36 (s, 3H), 3.76 (s, 3H), 4.41-4.46 (m, 1H), 5.61-5.73 (m, 2H), 7.11 (t, J=1.9 Hz, 1H); 13C NMR (50 MHz, CDCl3): δ 14.1, 23.8, 46.4, 51.9, 55.0, 55.4, 69.3, 95.9, 133.2, 148.3, 166.2, 184.9; Anal. Calcd for C12H17NO5 requires C, 56.46; H, 6.71; N, 5.49. Found: C, 56.51; H, 6.85; N, 5.48%.

Example 11

(3R,4R,5R)-ethyl 4-acetamido-5-hydroxy-3-(pentan-3-yloxy)cyclohex-1-enecarboxylate, (17)

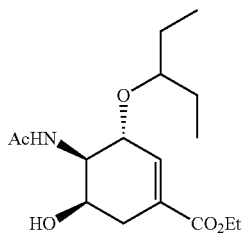 [SMILES: CCOC(=O)C1=C[C@@H](OC(CC)CC)[C@H](NC(C)=O)[C@H](O)C1]

To a well stirred solution of cyclic acetamide 16 (160 mg, 0.64 mmol) in 3-pentanol (10 mL), a solution of 1.5 equiv. BF3.Et2O (0.96 mmol) in 3-pentanol (2 mL) was added at −10° C., followed by stirring at this temperature for 30 minutes. After the completion of reaction (monitored by TLC), it was quenched with a saturated aq. solution of $K_2CO_3$. The organic layer was washed with $H_2O$, brine and dried over anhydrous $Na_2SO_4$. Removal of solvent under reduced pressure gave crude amino alcohol product of sufficient purity as a gum, which could be used for further reaction. To a well stirred solution of crude amino alcohol in EtOH (10 mL), a 2 N solution of HCl (2 mL) was added. The reaction was stirred for an additional 12 h at 25° C. After the completion of reaction (monitored by TLC), the reaction mixture was quenched by adding aqueous $K_2CO_3$. The reaction mixture was then partitioned between EtOAc and brine. The organic layer was further washed with brine, dried over anhydrous $Na_2SO_4$. Removal of solvent under reduced pressure gave crude product which on chromatographic purification with petroleum ether/ethyl acetate (2:8 v/v) gave title compound 17 as white solid. Yield: 64%; white solid; m.p. 129-131° C. {lit.4a m.p. 131.9-132.2° C.}; [α]D25 −83.8 (c 1.0, EtOAc) {lit.4a [α]D25 +104 (c 3, EtOAc)}; IR (CHCl3, cm-1): 1085, 1274, 1266, 1306, 1373, 1455, 1585, 1649, 1707, 2963, 3311, 3396 cm-1; 1H NMR (200 MHz, CDCl3): 0.90 (t, J=6.7 Hz, 6H), 1.25 (t, J=7.9 Hz, 3H), 1.42 (m, 4H), 1.99 (s, 3H), 2.59 (m, 2H), 3.40 (m, 1H), 3.46 (s, 1H), 3.86 (m, 1H), 3.91 (t, J=6.7 Hz, 1H), 4.15 (m, 3H), 4.41 (m, 1H), 5.78 (m, 1H), 6.84 (s, 1H); 13C NMR (50 MHz, CDCl3): δ 9.7, 9.8, 14.2, 23.8, 26.1, 26.7, 31.9, 55.2, 61.1, 67.4, 72.9, 82.3, 129.4, 136.4, 166.8, 171.8; Anal. Calcd for C16H27NO5 requires C, 59.46 requires C, 61.32; H, 8.68; N, 4.47. Found: C, 61.47; H, 8.71; N, 4.56%.

Example 12

(−)-Oseltamivir Free Base (1)

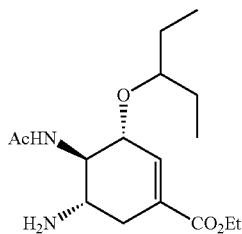 [SMILES: CCOC(=O)C1=C[C@@H](OC(CC)CC)[C@H](NC(C)=O)[C@@H](N)C1]

Compound 17 (312 mg, 1 mmol) and triethylamine (303 mg, 3 mmol) were dissolved in dry $CH_2Cl_2$ (15 mL), and the solution was cooled to 0° C. Methane sulfonyl chloride (229.2 mg, 2 mmol) was added, and the resulting solution was stirred at 0° C. for 1 h. After TLC indicated completion of reaction, further $CH_2Cl_2$ (20 mL) was added. The organic phase was washed with brine and then dried over anhydrous $Na_2SO_4$. After the solvent was removed by a rotavaporator, the crude product was dissolved in DMF and $NaN_3$ (390 mg, 6 mmol) was added. The reaction mixture was stirred at 80° C. for 3 h. After completion of reaction (monitored by TLC), the reaction mixture was partitioned between EtOAc and brine. The organic layer was further washed with brine, dried over anhydrous $Na_2SO_4$. Removal of solvent under reduced pressure gave crude product which on chromatographic purification with petroleum ether/ethyl acetate (4:6 v/v) gave the corresponding cyclic azide (this reaction is already known in literature) and the next reaction was done without the purification of cyclic azide. The cyclic azide was dissolved in EtOH and Lindlar's catalyst (20 mg) added. The reaction mixture was stirred for 6 h under a balloon of $H_2$ at room temperature and filtered through a celite pad. The filtrate was concentrated and the residue was purified by silica gel column chromatography using petroleum ether/ethyl acetate (7:3 v/v) as eluent to give (−)-oseltamivir free base as gum.

Yield: 64%; [α]D25 −47.8 (c 0.5, CHCl3) {lit.4a [α]D25 −54.2 (c 0.48, CHCl3)}; IR (CHCl3, cm-1): 1068, 1127, 1255, 1374, 1456, 1568, 1644, 1714, 2977, 3289 cm-1; 1H NMR (200 MHz, CDCl3): 0.90 (m, 6H), 1.31 (t, J=7.1 Hz, 3H), 1.42 (m, 4H), 2.03 (s, 3H), 2.23 (m, 1H), 2.76 (m, 1H), 3.30 (m, 1H), 3.46 (m, 1H), 4.15 (m, 3H), 5.78 (m, 1H), 6.79 (s, 1H); 13C NMR (50 MHz, CDCl3): δ 10.1, 10.2, 14.8, 24.5, 26.3, 26.7, 34.3, 49.8, 59.5, 61.3, 75.7, 82.3, 129.9, 138.0, 167.1, 171.8; Anal. Calcd for C16H28N2O4 requires C, 61.51; H, 9.03; N, 8.97. Found: C, 61.47; H, 8.98; N, 8.88%.

Example 13

(4S,5R)-methyl 3,4-dihydroxy-5-(methoxymethoxy)cyclohex-1-enecarboxylate, (19)

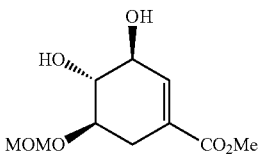

To a well stirred solution of compound 14 (107 mg, 0.5 mmol) in THF/H2O (3:1), concentrated $H_2SO_4$ (5 drops) was added. The reaction was stirred for 2 h at 25° C. After the completion of reaction (monitored by TLC), the reaction mixture was diluted with excess of EtOAc 20 mL The organic layer is further washed with $H_2O$, brine, dried over anhydrous $Na_2SO_4$. Removal of solvent under reduced pressure gave crude product which on chromatographic purification with petroleum ether/ethyl acetate (2:8 v/v) gave title compound 19 as gum.

Yield: 96%; thick liquid; [α]D25 −45.1 (c 0.5, EtOH); IR (CHCl3, cm-1): 1088, 1300, 1373, 1717, 2878, 2967, 3387, 3468; 1H NMR (200 MHz, CDCl3): 2.57-2.68 (m, 2H), 3.42 (s, 3H), 3.59 (m, 1H), 3.63 (m, 1H), 3.66 (s, 3H), 3.7 (m, 1H), 4.05 (m, 1H), 4.41 (m, 1H), 4.72 (s, 2H), 6.83 (s, 1H); 13C NMR (50 MHz, CDCl3): δ 30.9, 51.9, 55.8, 70.2, 77.6, 971, 127.9, 137.8, 166.6; Anal. Calcd for C10H16O6 requires C, 51.72; H, 6.94. Found C, 51.82; H, 6.98.

Example 14

Methyl 3-epi shikimate, (2)

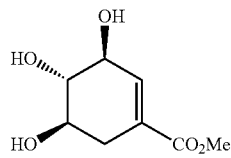 [SMILES: COC(=O)C1=C[C@H](O)[C@@H](O)[C@H](O)C1]

To a well stirred solution of compound 19 (95 mg, 0.5 mmol) in MeOH (5 mL) was added 2N solution of HCl (1 mL) The reaction was stirred for an additional 6 h at 25° C. After the completion of reaction (monitored by TLC), the reaction mixture was diluted with excess of EtOAc (10 mL). The organic layer was further washed with $H_2O$ (2 mL), brine, dried over anhydrous $Na_2SO_4$. Removal of solvent under reduced pressure gave crude product which on chromatographic purification with petroleum ether/ethyl acetate (2:8 v/v) gave title compound 2 in 74% yield as colorless solid.

Yield: 74%; white solid; m.p. 131-133° C. {lit.13 m.p. 132° C.}; $[\alpha]D25$ −13.1 (c 0.5, MeOH) {lit.13 $[\alpha]D25$ −13.4 (c 0.5, MeOH)}; IR (CHCl3, cm-1): 1089, 1176, 1245, 1378, 1489, 1661, 1714, 2106, 2994, 3456; 1H NMR (200 MHz, D2O): 2.23 (m, 1H), 2.81 (m, 1H), 3.47 (dd, J=8.5, Hz, 1H), 3.76 (s, 3H), 3.77 (m, 1H), 4.24 (m, 1H), 6.68 (m, 1H); 13C NMR (50 MHz, D2O): 168.6, 138.4, 127.2, 76.4, 71.9, 68.6, 52.8, 31.7; Anal. Calcd for C8H12O5 requires C, 51.06; H, 6.43; O, 42.51. Found C, 51.11; H, 6.54.

Advantages of the Present Invention

The present invention provides a new enantioselective method for the synthesis of anti-influenza agent (−)-oseltamivir and (−)-methyl 3-epi-shikimate from readily available starting materials using Sharpless asymmetric epoxidation, diastereoselective Barbier allylation and ring closing metathesis as key reactions. The synthesis has been completed with excellent enantiomeric excess (98% from HPLC) and good overall yield 7.1% and 16% for (−)-oseltamivir and (−)-methyl 3-epi-shikimate respectively.

In the present invention inexpensive and non-toxic reagents and viable reaction conditions have been used which makes our approach more feasible and attractive for commercial production.

We claim:

1. A process for the preparation of oseltamivir with enantioselectivity 98% ee and methyl 3-epi-shikimate, wherein the said process comprises:

(i) monosilylating of cis-1,4-butene diol (6) in a dry aprotic solvent and imidazole and a silylating agent at the temperature ranging between 0-25 deg C for a period ranging between 4-8 hours to obtain mono-silyl allylic alcohol (Z)-4-(tert-butyldimethylsilyloxy)but-2-en-1-ol (7):

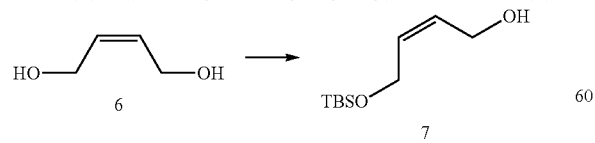

(ii) asymmetric epoxidizing mono-silyl allylic alcohol (Z)-4-(tert-butyldimethylsilyloxy)but-2-en-1-ol (7) with Ti(OiPr)4, (+) DET (diethyl tartarate), anhydrous TBHP (tert-butyl hydroperoxide) in a aprotic solvent at a temperature ranging between −10° C. C to −20° C. for a time period of 10 to 20 minutes to obtain epoxy alcohol ((2S,3R)-3-((tert-butyldimethylsilyloxy)methyl)oxiran-2-yl)methanol of formula (8) followed by oxidizing with TEMPO (2,2,6,6-tetramethyl-1-piperidinyloxyl)/BAIB[bis(acetoxy)iodo]benzene] mixture to obtain aldehyde2R,3R)-3-((tert-butyldimethylsilyloxy)methyl)oxirane-2-carbaldehyde of formula (9);

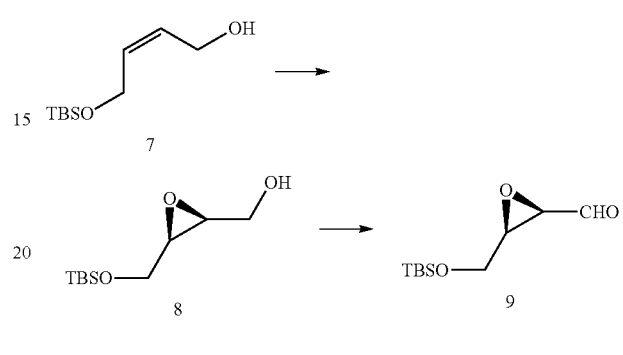

(iii) subjecting aldehyde (9) to diastereoselective Barbier allylation in the presence of ethyl 2-(bromomethyl)acrylate, Zn dust in an aprotic solvent and $NH_4Cl$ at the temperature ranging between 25-30° C. for a period of 8-12 hours to obtain the compound 10 ((R)-Ethyl 4-((2S, 3R)-3-((tert-butyldimethylsilyloxy)methyl)oxiran-2-yl)-4-hydroxy-2-methylenebutanoate):

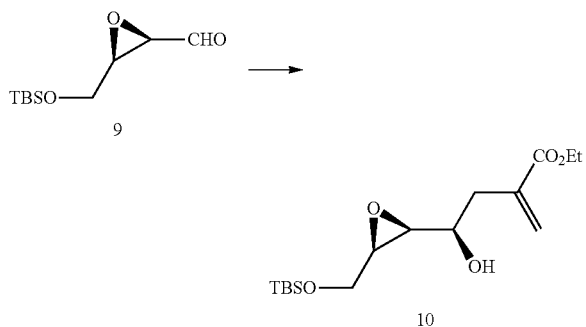

(iv) adding N,N-dipropylethylamine (hunig's base) to a solution of compound 10 as obtained in step (iii) in a dry aprotic solvent in the presence of a protecting agent at a temperature ranging between 0-25° C. for a period of 10-16 hours to obtain compound (R)-ethyl 4-((2S,3R)-3-((tert-butyldimethylsilyloxy)methyl)oxiran-2-yl)-4-(methoxymethoxy)-2-methylenebutanoate of formula 11 followed by desilylation using TBAF (tetrabutyl ammonium fluoride) to obtain compound 12:

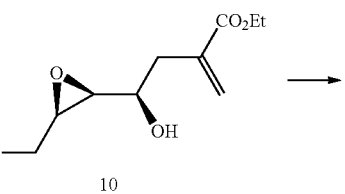

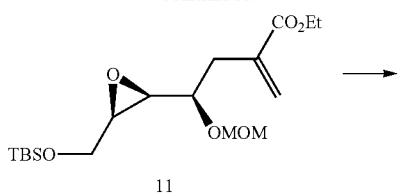

11

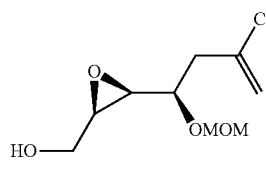

12

(v) oxidizing the compound 12 with an oxidizing agent IBX (2-iodoxy benzoic acid) and an aprotic solvent to obtain unstable aldehyde followed by subjecting to Seyferth-gilbert homologation in the presence of diethyl 2-oxopropylphosphonate, a base and a polar solvent at a temperature ranging between 0-25° C. for a time period ranging between 8-12 h to obtain the terminal alkyne (R)-methyl 4-((2S,3R)-3-ethynyloxiran-2-yl)-4-(methoxymethoxy)-2 methylenebutanoate of formula 13:

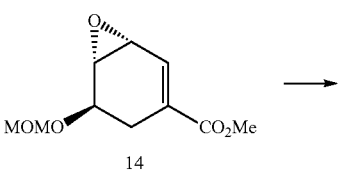

12

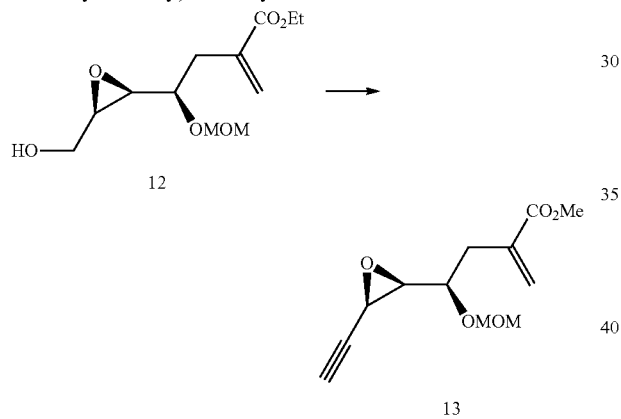

13

(vi) reducing the alkyne 13 with Lindlar's catalyst (Pd adsorbed on CaCO3) in an aprotic solvent at a temperature ranging between 25-30° C. for a time period ranging between 2-6 hours to obtain diene followed by ring closing metathesis using Grubb's IInd generation catalyst (1,3-Bis(2,4,6-trimethylphenyl)-2-imidazolidinylidene)dichloro(phenylmethylene)(tricyclohexylphosphine) ruthenium in dry aprotic solvent at a temperature ranging between 25-50° C. for a time period ranging between 14-24 hours to obtain epoxide compound (1R,5R,6S)-methyl 5-(methoxymethoxy)-7-oxabicyclo[4.1.0]hept-2-ene-3-carboxylate of formula 14:

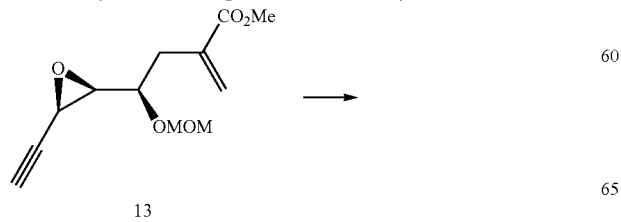

13

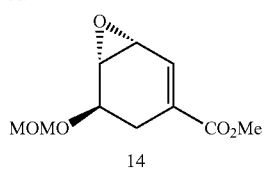

14

(vii) regioselective opening of epoxide compound 14 with NaN3 and mixture of solvent DMF:ethanol:water in the ratio of 1:1:0.5 to 2:2:1 at a temperature ranging between 25-30° C. for a time period of 10-12 hours to obtain compound (3S,4R,5R)-methyl 3-azido-4-hydroxy-5-(methoxymethoxy)cyclohex-1-enecarboxylate of formula 15:

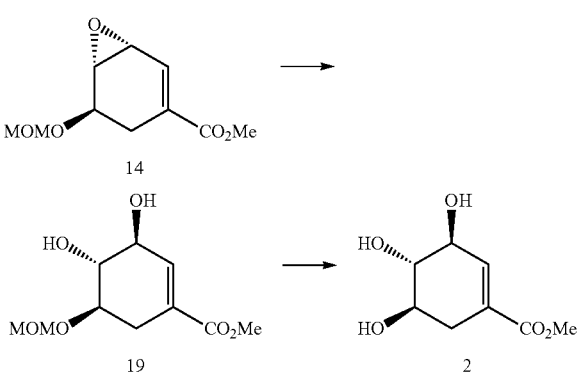

15

(viii) optionally treating cyclohexene epoxide (14) as obtained in step (vi) with sulphuric acid in THF:H2O in the ratio of 3:1 to 4:1 as solvent at a temperature ranging between 25 to 30° C. for a time period of 2 to 4 hrs to obtain diol compound 19 followed by deprotecting MOM of compound 19 with HCL in an alcohol at a temperature ranging between 25° C. to 30° C. for a time period of 6 to 8 hrs to obtain Methyl 3-epi shikimate(2):

(ix) aziridinizing the compound 15 as obtained in step (vii) with triphenyl phosphene (PPh3), toluene at 110° C. for a time period ranging between 3-12 hours to obtain a aziridine compound (1S,5R,6S)-methyl 7-acetyl-5-(methoxymethoxy)-7-azabicyclo[4.1.0]hept-2-ene-3-carboxylate, of formula 16:

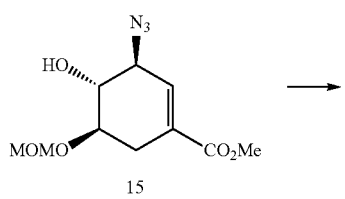

15

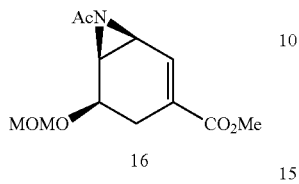

16

(x) regioselective ring opening of aziridine (16) with pentan-3-ol in the presence of BF3.Et2O at a temperature ranging between 0-25° C. for a time period ranging between 2-12 hours to obtain compound 17 followed by MOM deprotection in an alcohol and HCL at a temperature ranging between 25-30° C. for a time period of 4-12 hours to give compound 17 (3R,4R,5R)-Ethyl 4-acetamido-5-hydroxy-3-(pentan-3-yloxy)cyclohex-1-en-ecarboxylate; and

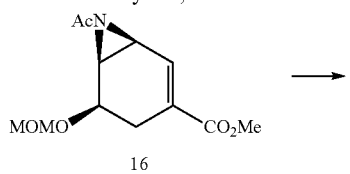

16

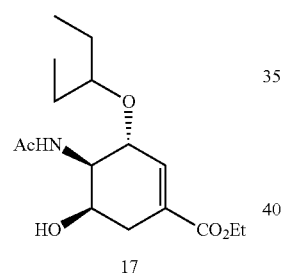

17

(xi) converting compound 17 to Oseltamivir

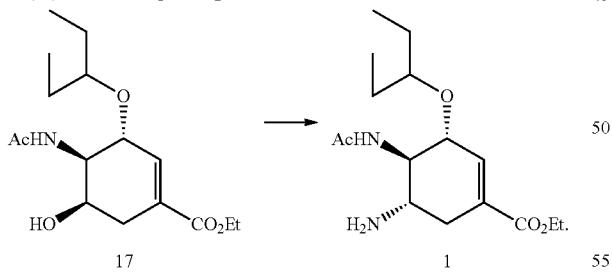

2. The process as claimed in claim 1, wherein the aprotic solvent and the polar solvent are each selected from the group consisting of toluene, acetone, ethyl acetate, methanol, THF, DCM, and DMSO.

3. The process as claimed in claim 1, wherein the silylating agent used in step (i) is selected from the group consisting of trimethylsilyl (TMS), tert-butyldiphenylsilyl (TBDPS), tert-butyldimethylsilyl (TBS/TBDMS) and triisopropylsilyl (TIPS), [2-(trimethylsilyl)ethoxy]methyl (SEM), and tert-butyl dimethylsilyl chloride (TBSCl).

4. The process as claimed in claim 1, wherein the base used in step (v) is selected from the group comprising consisting of $K_2CO_3$, and $Et_3N$.

5. The process as claimed in claim 1, wherein protecting agent used in step (iv) is MOMCl (methyl chloromethyl ether).

6. A compound of Formula 1

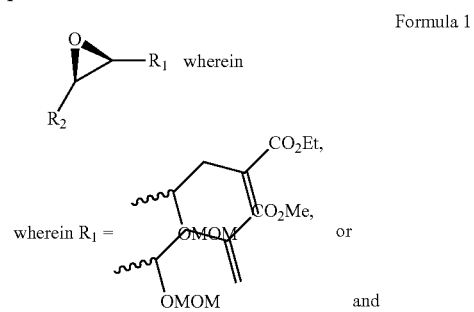

$R_2$=—$CH_2OTBS$, or —C≡CH.

7. The compound of claim 6, wherein the compound is selected from the group consisting of

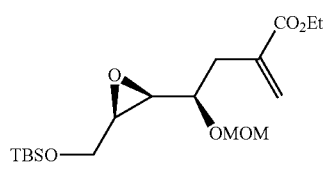

(R)-ethyl 4-((2S,3R)-3-((tert-butyldimethylsilyloxy)methyl)oxiran-2-yl)-4-(methoxymethoxy)-2-methylenebutanoate (Compound 11), and

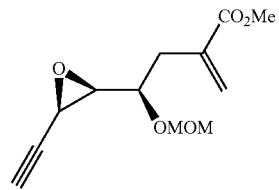

(R)-methyl 4-((2S,3R)-3-ethynyloxiran-2-yl)-4-(methoxymethoxy)-2-methylenebutanoate, (Compound 13).

8. A compound of Formula 2

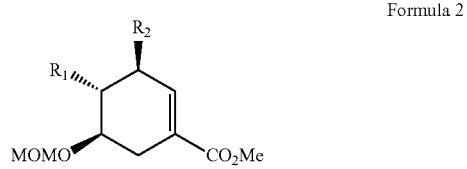

wherein $R_1$=OH and $R_2$=$N_3$; or R1+R2=O or NAc.

9. The compound of claim 8, wherein the compound is selected from the group consisting of

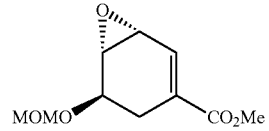

(1R,5R,6S)-methyl 5-(methoxymethoxy)-7-oxabicyclo[4.1.0]hept-2-ene-3-carboxylate, (Compound 14),

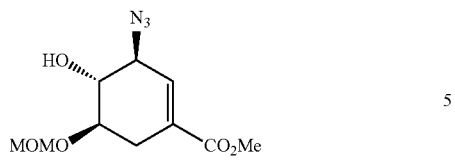
(3S,4R,5R)-methyl 3-azido-4-hydroxy-5-(methoxymethoxy)cyclohex-1-ene-carboxylate, Compound 15), and
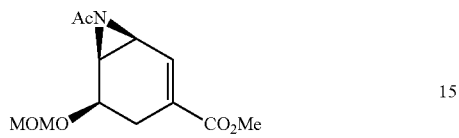
(1S,5R,6S)-methyl 7-acetyl-5-(methoxymethoxy)-7-azabicyclo[4.1.0]hept-2-ene-3-carboxylate (Compound 16).
* * * * *